US012121069B2

(12) United States Patent
Woodbine et al.

(10) Patent No.: US 12,121,069 B2
(45) Date of Patent: Oct. 22, 2024

(54) SYSTEM AND METHOD FOR METERED DOSING VAPORIZER

(71) Applicant: GoFire, Inc., Wheat Ridge, CO (US)

(72) Inventors: John Jesse Woodbine, Lafayette, CO (US); Stephen B. Katsaros, Denver, CO (US); Peter William Calfee, Englewood, CO (US)

(*) Notice: Subject to any disclaimer, the term of this patent is extended or adjusted under 35 U.S.C. 154(b) by 510 days.

(21) Appl. No.: 17/381,108

(22) Filed: Jul. 20, 2021

(65) Prior Publication Data

US 2021/0345677 A1    Nov. 11, 2021

Related U.S. Application Data

(63) Continuation of application No. 17/190,044, filed on Mar. 2, 2021, now Pat. No. 11,109,622.

(Continued)

(51) Int. Cl.
| | |
|---|---|
| *A24F 40/485* | (2020.01) |
| *A24F 40/10* | (2020.01) |
| *A24F 40/42* | (2020.01) |
| *A24F 40/46* | (2020.01) |
| *A24F 40/53* | (2020.01) |

(Continued)

(52) U.S. Cl.
CPC ............ *A24F 40/485* (2020.01); *A24F 40/10* (2020.01); *A24F 40/42* (2020.01); *A24F 40/46* (2020.01); *A24F 40/53* (2020.01); *A24F 40/65* (2020.01); *A61M 15/0021* (2014.02); *A61M 15/009* (2013.01); *A61M 15/06* (2013.01); *A24F 7/00* (2013.01); *A61M 2205/581* (2013.01)

(58) Field of Classification Search
CPC ........ A24F 40/485; A24F 40/48; A24F 40/40; A24F 40/42; A24F 40/10; A24F 40/65
See application file for complete search history.

(56) References Cited

U.S. PATENT DOCUMENTS

| | | | |
|---|---|---|---|
| 4,934,358 A | 6/1990 | Nilsson et al. | |
| 4,947,875 A | 8/1990 | Brooks et al. | |
| (Continued) | | | |

FOREIGN PATENT DOCUMENTS

| | | |
|---|---|---|
| EP | 2207528 | 10/2013 |
| EP | 3099363 | 12/2016 |

(Continued)

*Primary Examiner* — Hae Moon Hyeon
(74) *Attorney, Agent, or Firm* — Daniel W. Roberts; Law Offices of Daniel W. Roberts, LLC

(57) ABSTRACT

Provided is a system and method for a dosing vaporizer. More specifically, an embodiment of the system includes a housing with a first end opposite from a second end. A mouthpiece disposed proximate to the first end, the mouthpiece structured and arranged to rotate about the first end. An attacher disposed proximate to the second end, the attacher structured and arranged for removable attachment to a power source. A reservoir of liquid concentrate is disposed within the housing. A vaporizer disposed proximate to the attacher and thermally isolated from the reservoir. A vapor conduit passes generally from the vaporizer through the housing to the mouthpiece. A metered rotation driven dispenser, coupled to the mouthpiece, applies a predetermined force upon the reservoir to dispense from the reservoir into the vaporizer a predetermined amount of liquid concentrate.

34 Claims, 10 Drawing Sheets

Related U.S. Application Data

(60) Provisional application No. 63/002,131, filed on Mar. 30, 2020.

(51) Int. Cl.
*A24F 40/65* (2020.01)
*A61M 15/00* (2006.01)
*A61M 15/06* (2006.01)
*A24F 7/00* (2006.01)

(56) References Cited

U.S. PATENT DOCUMENTS

| | | |
|---|---|---|
| 5,284,133 A | 2/1994 | Burns et al. |
| 6,772,756 B2 | 8/2004 | Shayan |
| 6,814,083 B2 | 11/2004 | Likness et al. |
| 6,830,046 B2 | 12/2004 | Blakley |
| 7,088,914 B2 | 8/2006 | Whittle et al. |
| 7,164,993 B2 | 1/2007 | Likness et al. |
| 7,540,286 B2 | 6/2009 | Cross et al. |
| 7,905,230 B2 | 3/2011 | Schuler |
| 8,464,706 B2 | 6/2013 | Crockford et al. |
| 8,550,069 B2 | 10/2013 | Alelov |
| 8,602,037 B2 | 12/2013 | Inagaki |
| 8,851,068 B2 | 10/2014 | Cohen et al. |
| 8,897,628 B2 | 11/2014 | Conley et al. |
| 8,899,239 B2 | 12/2014 | Hon |
| 8,910,630 B2 | 12/2014 | Todd |
| 9,220,294 B2 | 12/2015 | McCullough |
| 9,320,301 B2 | 4/2016 | Memari et al. |
| 9,380,813 B2 | 7/2016 | McCullough |
| 9,462,832 B2 | 10/2016 | Lord |
| 11,109,622 B1 * | 9/2021 | Woodbine ............ A24F 40/46 |
| 2005/0277912 A1 | 12/2005 | John |
| 2006/0092071 A1 | 5/2006 | Andermo |
| 2006/0289005 A1 | 12/2006 | Jones |
| 2010/0250280 A1 | 9/2010 | Sutherland |
| 2011/0118694 A1 | 5/2011 | Yodfat |
| 2012/0029442 A1 | 2/2012 | Boyd |
| 2013/0220315 A1 | 8/2013 | Conley |
| 2013/0245545 A1 | 9/2013 | Arnold |
| 2013/0245604 A1 | 9/2013 | Kouyoumjian |
| 2013/0340775 A1 | 12/2013 | Juster |
| 2014/0000638 A1 | 1/2014 | Sebastian |
| 2014/0116455 A1 | 5/2014 | Youn |
| 2014/0202477 A1 | 7/2014 | Qi et al. |
| 2014/0243749 A1 | 8/2014 | Edwards et al. |
| 2014/0278250 A1 | 9/2014 | Smith et al. |
| 2014/0322782 A1 | 10/2014 | Baym |
| 2014/0345633 A1 | 11/2014 | Talon et al. |
| 2014/0345635 A1 | 11/2014 | Rabinowitz et al. |
| 2015/0039591 A1 | 2/2015 | Ding et al. |
| 2015/0053217 A1 | 2/2015 | Steingraber et al. |
| 2015/0136158 A1 | 5/2015 | Stevens et al. |
| 2015/0142387 A1 | 5/2015 | Alarcon et al. |
| 2015/0181945 A1 | 7/2015 | Tremblay |
| 2015/0245660 A1 | 9/2015 | Lord |
| 2015/0272220 A1 | 10/2015 | Spinka et al. |
| 2015/0297859 A1 | 10/2015 | Spandorfer |
| 2015/0320948 A1 | 11/2015 | Eicher |
| 2015/0327596 A1 | 11/2015 | Alarcon et al. |
| 2015/0332379 A1 | 11/2015 | Alarcon |
| 2015/0366266 A1 | 12/2015 | Shabat |
| 2016/0007651 A1 | 1/2016 | Ampolini et al. |
| 2016/0021930 A1 | 1/2016 | Minskoff et al. |
| 2016/0089508 A1 | 3/2016 | Smith et al. |
| 2016/0106935 A1 | 4/2016 | Sezan |
| 2016/0106936 A1 | 4/2016 | Kimmel |
| 2016/0143361 A1 | 5/2016 | Juster et al. |
| 2016/0157524 A1 | 6/2016 | Bowen et al. |
| 2016/0200463 A1 | 7/2016 | Hodges |
| 2016/0211693 A1 | 7/2016 | Stevens et al. |
| 2016/0219932 A1 | 8/2016 | Glaser |
| 2016/0219933 A1 | 8/2016 | Henry, Jr. et al. |
| 2016/0219938 A1 | 8/2016 | Mamoun et al. |
| 2016/0278435 A1 | 9/2016 | Choukroun et al. |
| 2016/0309784 A1 | 10/2016 | Silvestrini et al. |
| 2016/0309789 A1 | 10/2016 | Thomas, Jr. |
| 2016/0325058 A1 | 11/2016 | Samson |
| 2016/0331027 A1 | 11/2016 | Cameron |
| 2016/0331913 A1 | 11/2016 | Bourque |
| 2016/0337141 A1 | 11/2016 | Cameron |
| 2016/0356751 A1 | 12/2016 | Blackley |
| 2016/0363570 A1 | 12/2016 | Blackley |
| 2016/0363917 A1 | 12/2016 | Blackley |
| 2017/0014582 A1 | 1/2017 | Skoda |
| 2018/0177958 A1 | 2/2018 | Wilder |
| 2018/0160732 A1 * | 6/2018 | Bless .................... A24F 40/42 |
| 2018/0043114 A1 | 8/2018 | Shears |
| 2018/0263283 A1 | 9/2018 | Popplewell |
| 2018/0263288 A1 | 9/2018 | Goldstein |
| 2018/0353682 A1 | 12/2018 | Laurence |
| 2019/0111220 A1 | 4/2019 | Richardson |
| 2019/0325287 A1 | 10/2019 | Strange |
| 2020/0060342 A1 * | 2/2020 | Woodbine ......... A61M 15/0065 |
| 2020/0120989 A1 * | 4/2020 | Danek ................ A61K 9/0073 |

FOREIGN PATENT DOCUMENTS

| | | |
|---|---|---|
| EP | 3102266 | 12/2016 |
| GB | 2524779 | 10/2015 |
| WO | WO03097141 | 11/2003 |
| WO | WO2016050247 | 4/2016 |
| WO | WO2016064906 | 4/2016 |
| WO | WO2016172802 | 11/2016 |
| WO | WO2016187695 | 12/2016 |

* cited by examiner

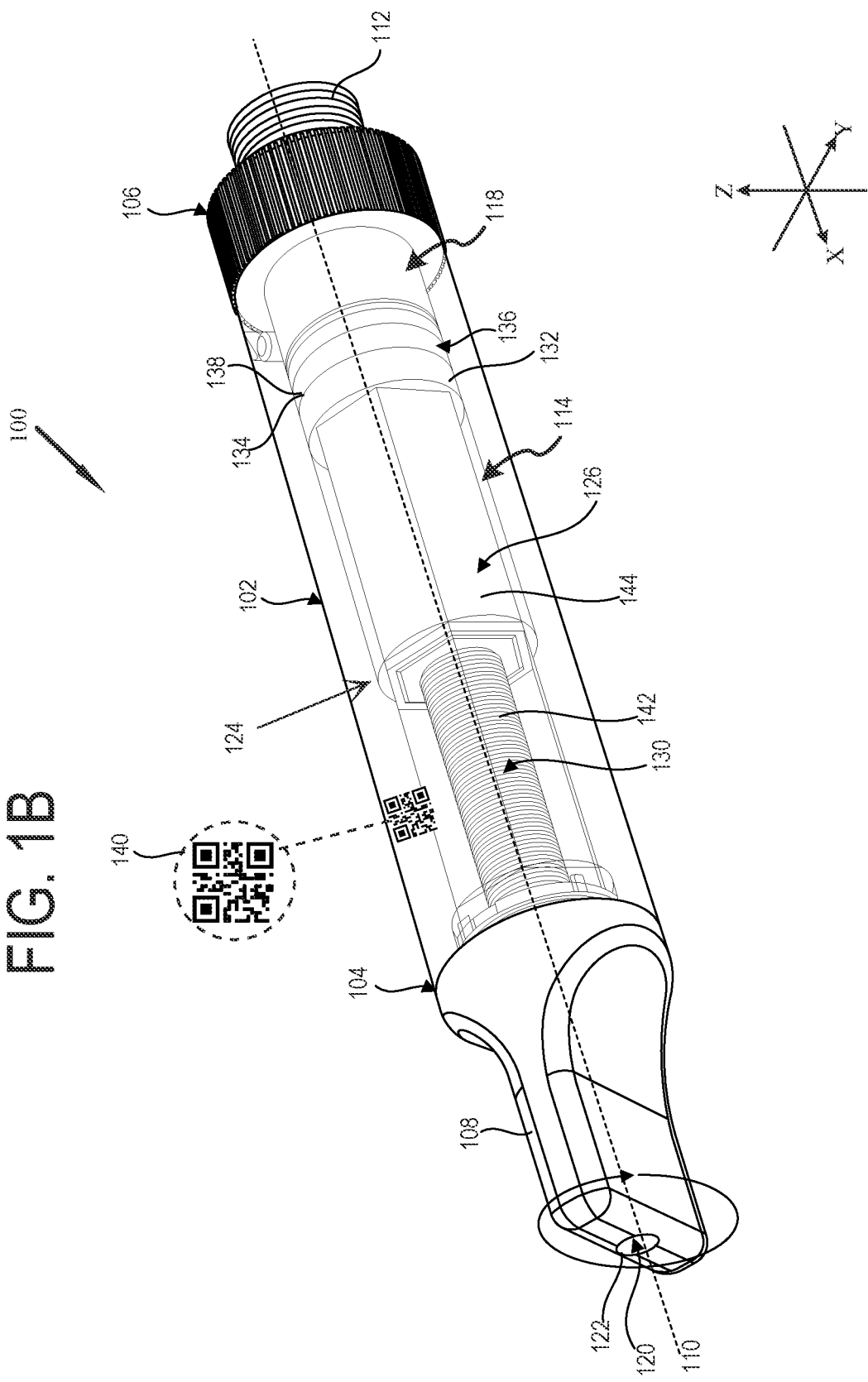

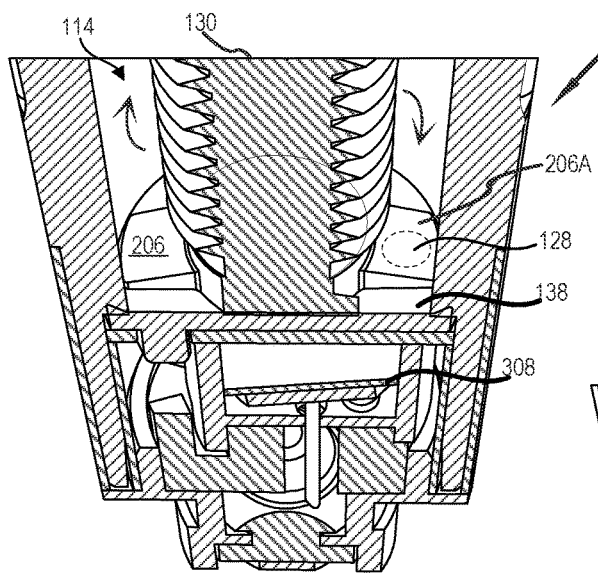
FIG. 4A
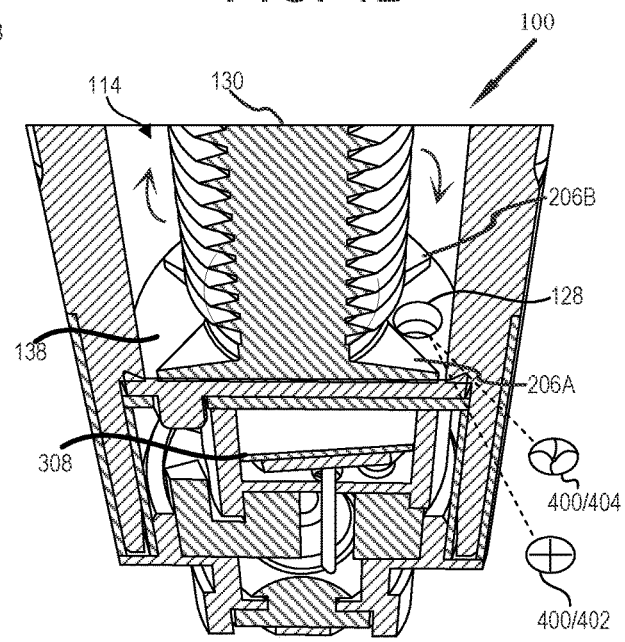
FIG. 4B
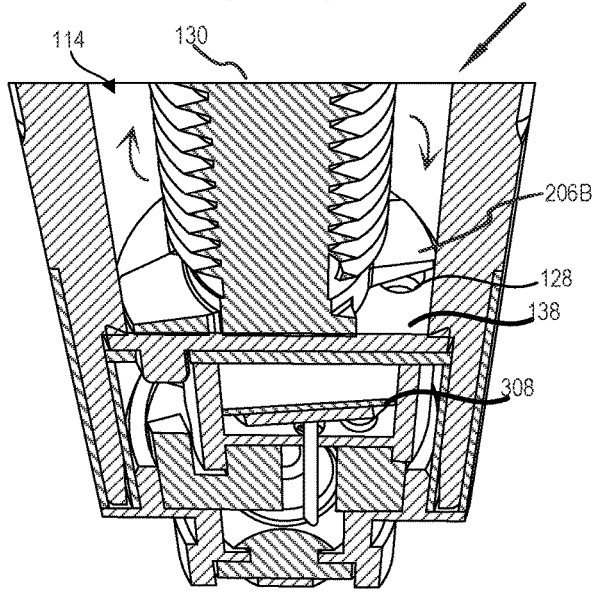
FIG. 4C
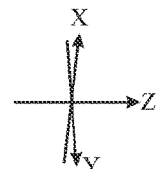

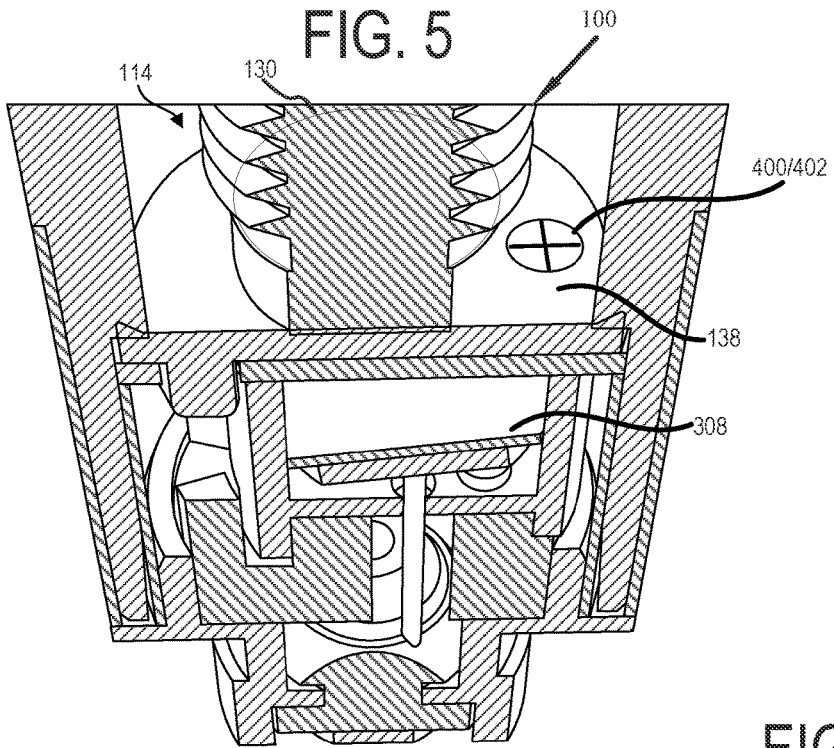
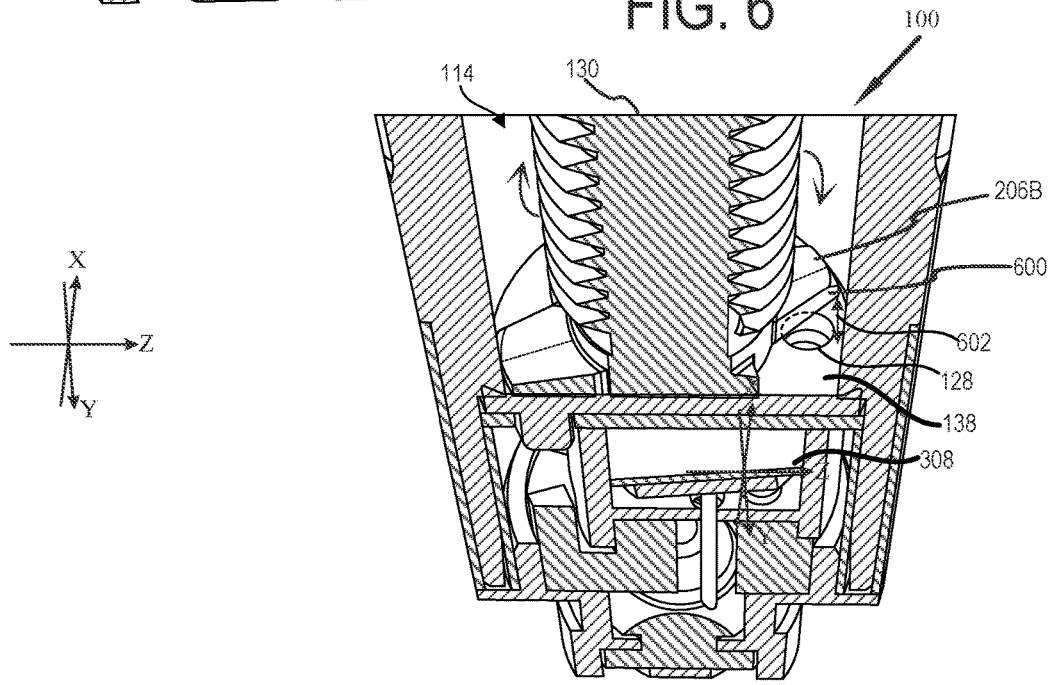

SYSTEM AND METHOD FOR METERED DOSING VAPORIZER

CROSS REFERENCE TO RELATED APPLICATIONS

This application is a continuation of U.S. patent application Ser. No. 17/190,044 filed Mar. 2, 2021, now U.S. Pat. No. 11,109,622, entitled SYSTEM AND METHOD FOR DOSING VAPORIZER and incorporated by reference. This continuing application claims the benefit of U.S. patent application Ser. No. 17/190,044 which in turn claimed the benefit under 35 U.S.C. § 119(e) of U.S. Provisional Application No. 63/002,131 filed Mar. 30, 2020 and entitled SYSTEM AND METHOD FOR DOSING VAPORIZER, the disclosure of which is incorporated herein by reference.

In addition, the following patent applications and patents are incorporated by reference herein in their entireties: U.S. patent application Ser. No. 15/391,829 entitled SYSTEM AND METHOD FOR MANAGING CONCENTRATE USAGE OF A USER (hereinafter "'829 App"), U.S. patent application Ser. No. 16/592,674 entitled SYSTEM AND METHOD FOR MANAGING CONCENTRATE USAGE OF A USER (hereinafter "'674 App"), U.S. Patent Application Ser. No. 62/660,974 entitled SMART VAPORIZER AND SYSTEM FOR CONCENTRATE PRODUCTS (hereinafter "'974 App"), U.S. Patent Application Ser. No. 62/721,699 entitled VAPORIZER CARTRIDGE SYSTEM AND METHOD OF USE (hereinafter "'699 App"), U.S. patent application Ser. No. 16/541,062 entitled SYSTEM AND METHOD FOR VAPORIZING CARTRIDGE SYSTEM WITH DIFFUSER (hereinafter "'062 App"), U.S. patent application Ser. No. 16/559,556 entitled SYSTEM AND METHOD FOR DETERMINING AN APPROPRIATE DOSE OF A PRODUCT (hereinafter "'556 App"), and U.S. Pat. No. 10,888,665 entitled SYSTEM AND METHOD FOR MULTI-MODAL DOSING DEVICE (hereinafter "'665 Patent"), U.S. Pat. No. 10,888,666 entitled SYSTEM AND METHOD FOR MULTI-MODAL DOSING DEVICE (hereinafter "'666 Patent"), and U.S. Pat. No. 10,834,967 entitled SYSTEM AND METHOD FOR MANAGING CONCENTRATE USAGE OF A USER (hereinafter "'967 Patent").

FIELD OF THE INVENTION

The present invention relates generally to a dosing vaporizer system structured and arranged so as to provide a dose of a given product in an inhalable form to a user. The product is generally understood to be a liquid or oil concentrate. In particular, the present invention presents a system for the precise dosing of a product by providing a self-contained vaporizer, reservoir, and dosing system.

BACKGROUND

Often referred to as e-cigarettes, hand held vaporizers, "vapes" or the like, the general device is understood and appreciated to be a hand-held electronic device that provides a user with a vapor for medical or recreational inhalation In general, these devices are generally understood to comprise an electrically activated vaporizer, within a housing that provides a mouthpiece and typically encloses a cartridge or reservoir of the material to be vaporized.

For some models the battery powering the vaporizer may be removable, while in others it is permanent. Of course, the batteries may be rechargeable as well.

With a traditional smoking device where fire is used to combust a material into smoke, as with a pipe, cigarette or cigar, the inhalation by the user draws air through the burning medium which furthers the burning action, and creates the draw of smoke.

With vaporizer devices, although the draw of air by the user may be used to trigger device operation, the transition of the inhaled substance from an initial state to a vapor state is not accomplished by fire. Most commonly, the material to be vaporized is provided in a liquid form—such as an oil based liquid, that serves as a transport medium to initially store the inhalant compound, and later convey the inhalant compound into a vaporizer element such that the liquid is transformed into a vapor for inhalation by the user.

Because of differing product characteristics current vaporizer solutions may or may not involve additional thinning agents—i.e., propylene glycol, vegetable glycerin, etc. More specifically, many products utilized in vaporizers rely upon a thinning agent in order to efficiently transport product to the vaporizer element—such as a heating coil in contact with or closely adjacent to a ceramic or metallic surface upon which the solution for vaporization is deposited.

With the increasing proliferation of plant based medicinal products, proper dosage is an important part of patient care for consistent and reliable treatment of a given condition or ailment. Indeed, in some cases different dosages of the same product may be appropriate for different conditions or ailments, thus further emphasizing the importance of proper product dosing for a specific condition or ailment.

Some vaporizing devices have intentionally positioned the reservoir of concentrate close to the heating element of the vaporizer, or other heating element so as to intentionally heat the concentrate within the reservoir/cartridge, so as to facilitate easy flow or wicking of the concentrate into the vaporizing element. In some cases, heating coils have even been disposed within or around at least a portion of the reservoir.

Although this was initially believed to be helpful, it has been realized that this additional and repeated heating can degrade the concentrate material leading to a breakdown or chemical change of the concentrate. This breakdown may result in decreased effectiveness and/or enjoyment of the vaporized concentrate, as well as other issues that are only just now being realized within the vaporization industry. Furthermore, the wick material, typically cotton, breaks down over use and has a negative impact on the flavor of the vapor.

As the vapor is provided from a liquid, not a burning product, it is also appreciated that the concentration of the inhalant, nicotine, CBD, or other compound, is largely dependent on the concentration provided in the liquid, and how much of that liquid is then dispensed and vaporized. Indeed, without accurate dispensing great variation from one vaporization to the next may occur.

Further, as variations of concentration may exist from one batch or manufacturer to another, precise dispensing, or dosing, is an important factor in reliable and repeatable vaporizing device usage. Moreover, for a given cartridge or reservoir of a vaporizable concentrate or product, for the using party to appreciate the benefits as truly intended it is highly desirable for the vaporizing system to achieve the same vaporizing affect upon all doses administered from the cartridge or reservoir, unless or until the user or other party intentionally directs a change, such as an alteration of dosing quantity, vaporizing temperature, vaporizing duration, etc.

Although some devices have attempted to provide dosage and vaporization based on inhalation as with a traditional smoking experience, such devices are subject to wild variability as the user may be completely unaware and unable to adjust the concentration of the product within the liquid suspension.

Hence there is a need for a method and system that is capable of overcoming one or more of the above identified challenges.

SUMMARY OF THE INVENTION

Our invention solves the problems of the prior art by providing a novel dosing vaporizer system to provide controlled dosage delivery of the product, while maintaining the integrity of the yet to be used product in a safe and efficacious manner.

In particular, and by way of example only, according to at least one embodiment, provided is a metered dosing vaporizer system including: a housing providing a first end and opposite thereto a second end; a mouthpiece disposed proximate to the first end, the mouthpiece structured and arranged to rotate about the first end; an attacher disposed proximate to the second end, the attacher structured and arranged for removable attachment to a power source; a reservoir of liquid concentrate within the housing; a vaporizer disposed proximate to the attacher and thermally isolated from the reservoir; a vapor conduit passing generally from the vaporizer, through the housing to the mouthpiece; and a metered rotation driven dispenser structured and arranged to apply a predetermined force upon the reservoir to dispense from the reservoir into the vaporizer a predetermined amount of liquid concentrate, wherein the metered rotation driven dispenser is coupled to the mouthpiece.

In yet another embodiment, provided is a metered dosing vaporizer system including: a housing providing a first end and opposite thereto a second end; a mouthpiece disposed proximate to the first end, the mouthpiece structured and arranged to rotate about the first end; a 510 battery connector disposed proximate to the second end, the battery connector structured and arranged for removable attachment to a battery; a reservoir of liquid concentrate within the housing; a vaporizer disposed proximate to the 510 battery connector and thermally isolated from the reservoir; a central vapor conduit passing generally from the vaporizer, through the housing to the mouthpiece; an aperture disposed between the reservoir and the vaporizer; and a screw plunger structured and arranged to apply a predetermined force upon the reservoir to dispense from the aperture a predetermined amount of liquid concentrate into the vaporizer, the rotation of the mouthpiece inducing a degree of rotation to the screw plunger, the degree of rotation pre-selected to advance the plunger against the liquid concentrate of the reservoir to dispense the predetermined amount of the liquid concentrate.

For yet another embodiment, provided is a metered dosing vaporizer system including: a handheld device having a first end and opposite thereto a second end, with a longitudinal axis therebetween; the first end defined by a mouthpiece structured and arranged for one way rotation about the longitudinal axis; the second end defined by an attacher, structured and arranged for removable attachment to a power source; a housing disposed between the mouthpiece and the attacher, the housing at least partially enclosing: a reservoir of liquid concentrate; a vaporizer disposed proximate to the attacher and thermally isolated from the reservoir; a vapor conduit coupling the vaporizer to the mouthpiece; a metered dispenser structured and arranged to dispense from the reservoir into the vaporizer a predetermined amount of liquid concentrate upon a pre-selected degree of rotation of the mouthpiece; and an activator, structured and arranged to activate the vaporizer by permitting a connection between the vaporizer and the power source for a first period of time, the power permitting the vaporizer to generate heat and vaporize the predetermined amount of liquid concentrate dispensed.

For still yet another embodiment, provide is a metered dosing vaporizer system including: a housing providing a first end and opposite thereto a second end; a mouthpiece disposed proximate to the first end, the mouthpiece structured and arranged for one way rotation about the first end; a removable power source disposed proximate to the second end; a reservoir of liquid concentrate within the housing; a vaporizer disposed proximate to the power source and thermally isolated from the reservoir; a central vapor conduit passing generally from the vaporizer, through the housing to the mouthpiece; and a metered rotation driven dispenser structured and arranged to apply a predetermined force upon the reservoir to dispense from the reservoir into the vaporizer a predetermined amount of liquid concentrate, the metered rotation driven dispenser coupled to the mouthpiece.

And further still, for another embodiment, provided is a method for vaporizing a metered dose of a product, including: providing a housing providing; a first end and opposite thereto a second end; a mouthpiece disposed proximate to the first end, the mouthpiece structured and arranged to rotate about the first end; an attacher disposed proximate to the second end, the attacher structured and arranged for removable attachment to a power source; a reservoir of liquid concentrate within the housing; a vaporizer disposed proximate to the attacher and thermally isolated from the reservoir; an vapor conduit passing generally from the vaporizer, through the housing to the mouthpiece; a metered rotation driven dispenser structured and arranged to apply a predetermined force upon the reservoir to dispense from the reservoir into the vaporizer a predetermined amount of liquid concentrate, the metered rotation driven dispenser coupled to the mouthpiece; rotating the mouthpiece to activate the metered rotation driven dispenser to dispense a predetermined amount of liquid concentrate into the vaporizer; and activating the vaporizer to vaporize the dispensed liquid concentrate into a vapor that is provided to a user through the mouthpiece.

BRIEF DESCRIPTION OF THE DRAWINGS

FIGS. 1A & 1B illustrate perspective views of embodiments of a Metered Dosing System Vaporizer in an initial state and a depleted state in accordance with at least one embodiment of the present invention;

FIGS. 4A, 4B and 4C provide partial cut through perspective sections of the Metered Dosing System Vaporizer shown in FIG. 2 further illustrating the shutter in operation in accordance with at least one embodiment of the present invention;

FIG. 5 presents a partial side perspective view of an embodiment of Metered Dosing System Vaporizer having a valve in place of a shutter in accordance with at least one embodiment of the present invention;

FIG. 6 presents a partial side perspective view of an embodiment of Metered Dosing System Vaporizer as shown in FIGS. 3A-3C wherein the leading edge of the shutter fin is raised in accordance with at least one embodiment of the present invention;

DETAILED DESCRIPTION

Before proceeding with the detailed description, it is to be appreciated that the present teaching is by way of example only, not by limitation The concepts herein are not limited to use or application with a specific dosing vaporizer system. Thus, although the instrumentalities described herein are for the convenience of explanation shown and described with respect to exemplary embodiments, it will be understood and appreciated that the principles herein may be applied equally in other types of systems involving dosing vaporizer systems.

This invention is described with respect to preferred embodiments in the following description with reference to the Figures, in which like numbers represent the same or similar elements. Further, with respect to the numbering of the same or similar elements, it will be appreciated that the leading values identify the Figure in which the element is first identified and described, e.g., element 100 first appears in FIG. 1.

Figure 1A:
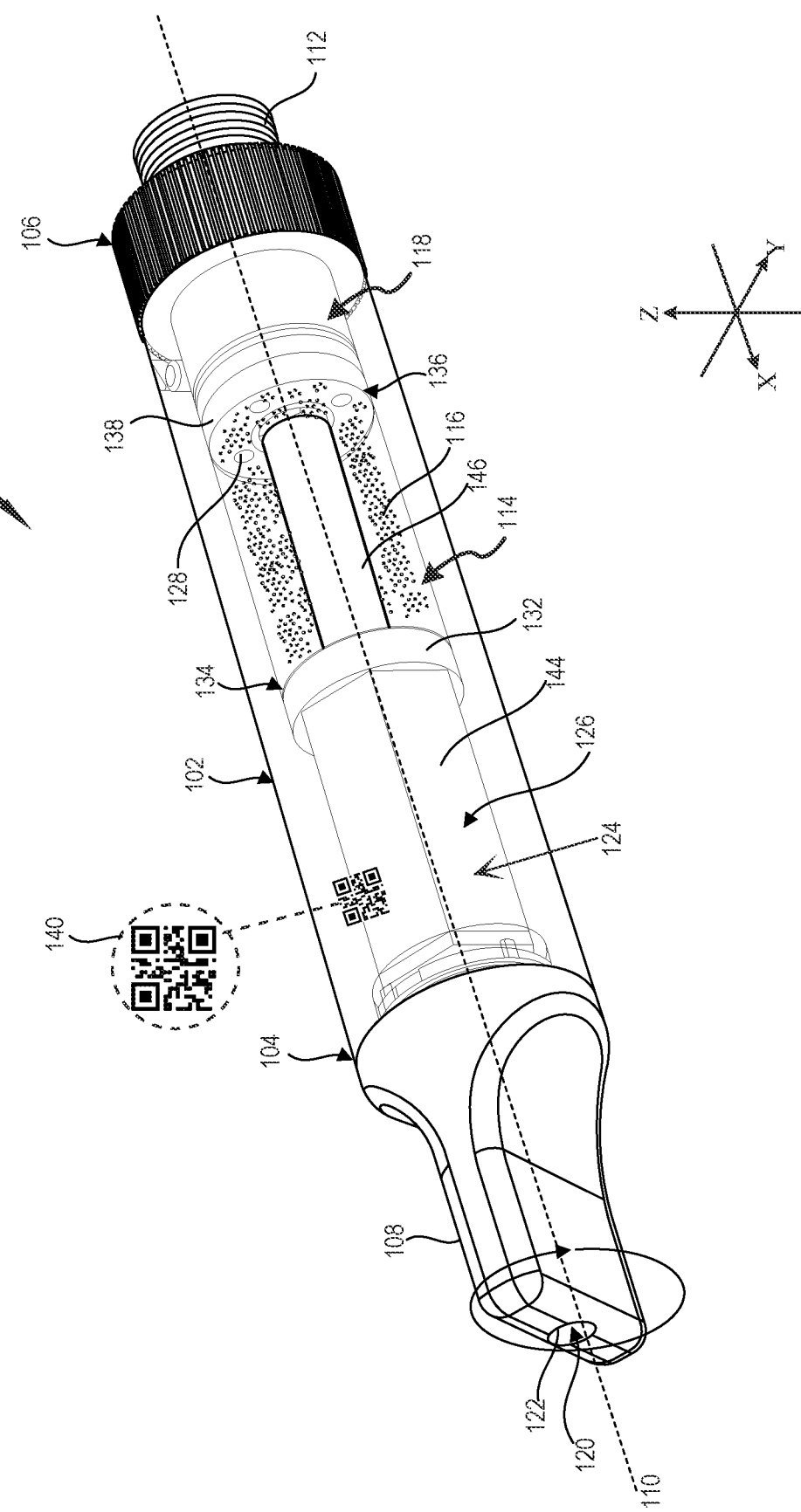

Turning now to the figures, FIGS. 1A and 1B which show two perspective views of at least one embodiment for a Metered Dosing System vaporizer, hereinafter MDSV 100. FIG. 1A, the top view, being an initial state of MDSV 100, and the bottom FIG. 1B being a final/depleted state of MDSV 100.

To facilitate the description of systems and methods for this MDSV 100 the orientation of MDSV 100, as presented in the figures, is referenced to the coordinate system with three axes orthogonal to one another as shown in FIG. 1. The axes intersect mutually at the origin of the coordinate system, which is chosen to be the center of MDSV 100, however the axes shown in all figures are offset from their actual locations for clarity and ease of illustration.

As shown, for at least one embodiment, the MDSV 100 is provide at least in part by a housing 102 providing a first end 104 and opposite thereto a second end 106. A mouthpiece 108 is disposed proximate to the first end 104, and structured and arranged to rotate about the first end 104. More specifically, MDSV 100 may be appreciated to have a longitudinal axis 110, the mouthpiece 108 rotating about the first end 104 with respect to the longitudinal axis 110.

An attacher 112 is disposed proximate to the second end 106 and is structured and arranged for removable attachment to a power source, such as a battery, not shown. As is further described below, for at least one embodiment the attacher 112 is a threaded coupling. In alternative embodiment, the attacher 112 is a snap-on coupling. Moreover, as oppose to devices which incorporate a power source within their structure, it is to be appreciated that embodiments of MDSV 100 are intended to be removably coupled to a remote power source such as a battery, and more specifically for some embodiments a 510 type battery. The removal of the battery from the internal or integrated components of MDSV 100 advantageously simplifies many factors, including but not limited to cost of fabrication, weight for shipping, and issues as may be associated with the safety and transport of some types of batteries. In addition, as the MDSV 100 and power source are separate elements, a battery is not potentially wasted simply because the MDSV 100 has been depleted, and likewise, MDSV 100 is not potentially wasted because the power source has been exhausted.

Within the housing 102 is shown a reservoir 114 of liquid concentrate 116. The term "concentrate," as used herein, may include substances in the form of chemicals, distillates, and isolates. Moreover, as used herein, the terms "liquid concentrate," "concentrate," "extruded liquid concentrate," un-dispensed concentrate," "different liquid concentrates" and variants thereof simply refer to fluid contained in the reservoir 114 and are therefore (in most instances) interchangeable. Examples of the liquid concentrate include vaporizable pharmaceuticals or medications, such as tetrahydrocannabinol (THC), terpenes, cannabidiol (CBD), and other constituents of cannabinoids, as well as substances based on, or containing, nicotine. In many instances, the liquid concentrate 116 may be of a type wherein exposure to air is undesirable for a variety of reasons, including but not limited to drying and oxidation. As such, it is an aspect of at least one embodiment of the present invention to provide an air tight seal for reservoir 114 so as to preserve the liquid concentrate 116 therein.

For the sake of ease of illustration and discussion, the concentrate 116 is represented by dots, however the space between dots is not intended to show or indicate a lack of concentrate 116 within the reservoir 114. For at least one embodiment the concentrate 116 is understood and appreciated to be a liquid concentrate. It will be further understood and appreciated that the liquid concentrate 116 may have a viscosity ranging from very low, a centipoise at or less than 1 (e.g., water) to very high, a centipoise at or above 100,000 (e.g. a paste). For at least one embodiment the liquid concentrate 116 is a nicotine liquid concentrate. For at least one alternative embodiment the liquid concentrate 116 is a CBD liquid concentrate. For yet another embodiment the liquid concentrate 116 is a pharmaceutical liquid concentrate.

As shown in FIGS. 1A and 1B, a vaporizer 118 is also disposed proximate to the attacher 112. As used herein, it will be understood and appreciated that "vaporizer" is a device, component or assemblage of parts that are structured and arranged to vaporize/atomize a liquid provided by the reservoir 114 into a vapor for inhalation through the mouthpiece 108. Embodiments of a vaporizer 118 are more fully set forth below with respect to FIG. 2.

As is further set forth below, in varying embodiments the vaporizer 118 may be a ceramic or other thermal material configured as a heating chamber or platform. For at least one embodiment the heating chamber or platform may be configured with a heating coil disposed therein. The heating chamber or platform may also be configured as an area providing a screen, mesh or other thermally conductive porous material into which the liquid concentrate 116 is disposed and dispersed.

Whether the liquid concentrate 116 is dispensed/dispersed into, onto or across the various chamber or platform elements, energy, typically in the form of heat, is applied by an electric heater proximate thereto, or other element which is structured and arranged to vaporize a dispensed quantity of the liquid concentrate 116 into a vapor which is then provided to the user through a vapor conduit 120 presenting to an opening 122 in the mouthpiece 108.

It will be understood and appreciated that the heating element itself may be incorporated as an integral component of the of the heating chamber or platform such that the same element receiving the dispensed liquid concentrate is also primarily responsible for achieving the vaporization thereof. Sonic or vibratory nebulization, or the like, may also be suitable in various embodiments, as well as infrared energy such as may be provided from a light source, such as but not limited to a diode.

As the vaporizer 118 is shown proximate to the attacher 112 and opposite from the mouthpiece 108, it is appreciated that within MDSV 100 is a vapor conduit 120 passing generally from the vaporizer 118 through the housing 102 to the mouthpiece 108. For at least one embodiment, the vapor conduit 120 is disposed substantially along the longitudinal axis 110. For yet another embodiment, the vapor conduit 120 may be disposed to one side of the inside of the housing 102, or as a series of conduits that are in varying combinations, central and or along the sides.

A metered rotation driven dispenser 124 is also shown, disposed within the housing 102, and structured and arranged to apply a predetermined force upon the reservoir 114 to dispense from the reservoir 114 into the vaporizer 118 a predetermined amount of liquid concentrate 116. It will be appreciated that the metered rotation driven dispenser 124 is coupled to the mouthpiece 108, such that rotation of the mouthpiece 108 drives the metered rotation driven dispenser 124. It will also be understood and appreciated from the figures that rotation of the mouthpiece 108 is generally about the longitudinal axis 110.

It will also be appreciated that MDSV 100 is a portable device and is intended for handheld use and operation by a human user. As used herein "handheld" will be understood and appreciated as designed to be held and used by hand FIG. 1A represents an initial state of MDSV 100 with the reservoir 114 essentially full of liquid concentrate 116. In FIG. 1B, the mouthpiece 108 has been rotated many times and the screw shaft 130 is now exposed to further illustrate that the screw plunger 126 has advanced down such that the threaded shaft of the screw plunger is now exposed to further illustrate that the rotation driven dispenser has advanced down and expelled substantially all of the liquid concentrate 116 from the reservoir 114—the MDSV 100 now being in a depleted state.

It will further be understood and appreciated, that the rotation of the mouthpiece 108 is limited to one direction: that is, for at least one embodiment the mouthpiece 108 can only be rotated clockwise, such that the metered rotation driven dispenser 124 cannot be backed up. Of course, for at least one alternative embodiment, the mouthpiece 108 can also be configured for counter-clockwise rotation to drive the metered rotation driven dispenser 124. Moreover, the rotation may be either clockwise or counter-clockwise, but not both.

Those skilled in the art will appreciate that as the metered rotation driven dispenser is an active mechanical device, it actively provides accurate and repeatable dispensation of consistently known quantities of the liquid concentrate 116 from the reservoir 114 by extrusion. This is in sharp contrast to, and highly advantageous over, many conventional systems which rely on the passive property of a wick to passively draw concentrate from a reservoir by capillary action.

In varying embodiments, MDSV 100 may provide a unique identifier 140, that may be scanned, read, or otherwise interpreted by a user, or a computing device such as a smart phone in the user's possession. The unique identifier may be provided to advantageously identify the MDSV 100 as well as specifically identify the liquid concentrate 116 contained therein. The unique identifier may be a compound element providing general or group information, e.g., company or DVS 100 model, as well as a unique component that may serve to uniquely identify the MDSV 100, user, liquid concentrate 116, or such other information as may be deemed relevant. For at least one embodiment, the unique identifier 140 is correlated to at least one database for the information associated therewith.

With respect to FIGS. 1A and 1B, it will be appreciated that the threads 142 of the screw shaft 130 are disposed above the reservoir 114 with the plunger seal 132 having a spacer 144 to permit the threads 142 to remain removed from the reservoir 114. For the embodiment of MDSV 100 as shown in FIGS. 1A and 1B, the vapor conduit 120 passes through the screw shaft 130. For at least one embodiment, the lower portion 146 of the screw shaft 130 that is disposed through the reservoir 114 (See FIG. 1A) will rotate as well when the mouthpiece 108 is rotated, which as described in furth detail below may facilitate the operation of a shutter to alternatively expose and seal the aperture 128. For yet another embodiment, what appears as the lower portion 146 of the screw shaft is a separate tube structure aligned with, and fluidly coupled to, the screw shaft 130.

Figure 2A:
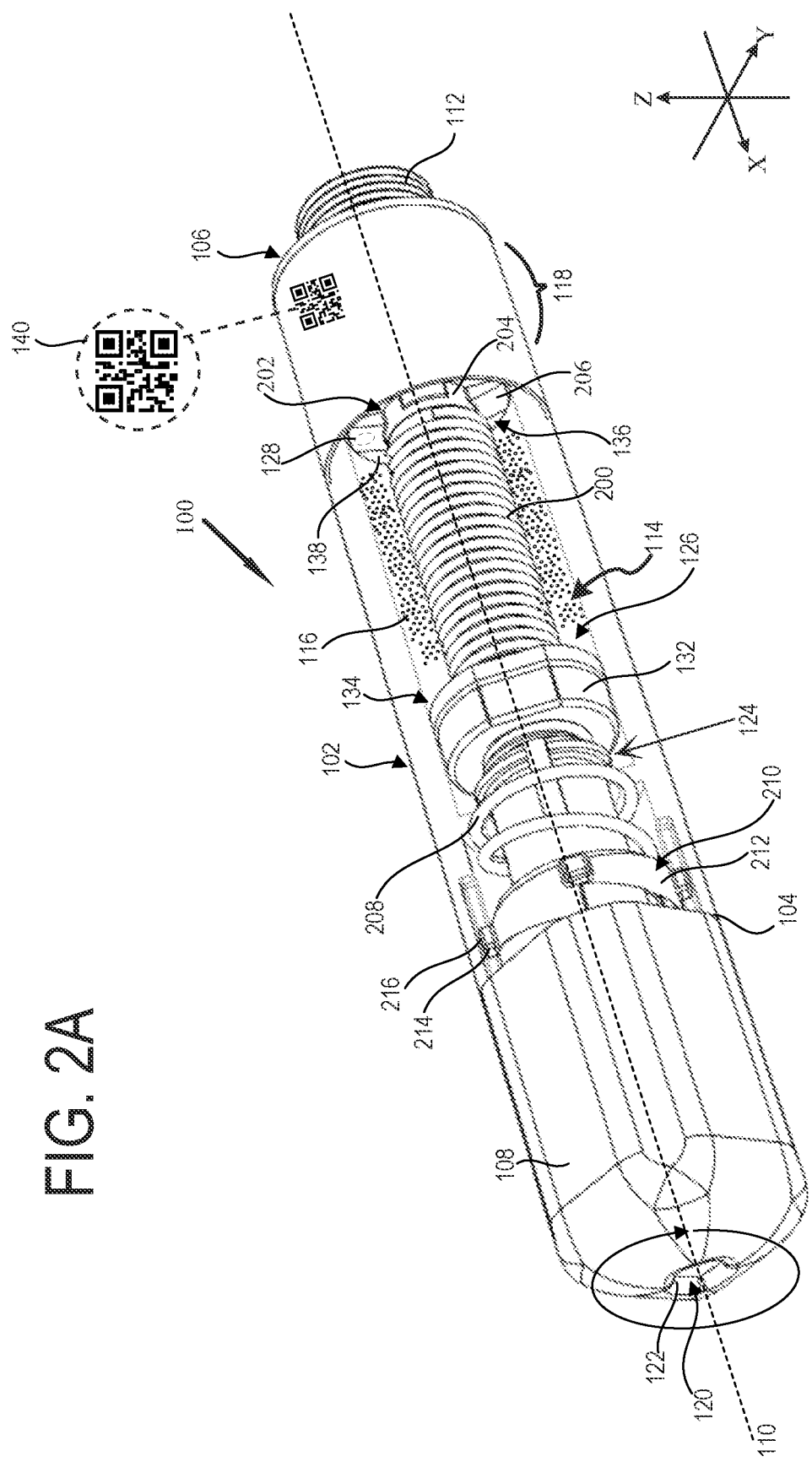
FIGS. 2A & 2B illustrate perspective views of yet other embodiments of a Metered Dosing System Vaporizer in an initial state and a depleted state in accordance with at least one embodiment of the present invention.
Figure 2B:
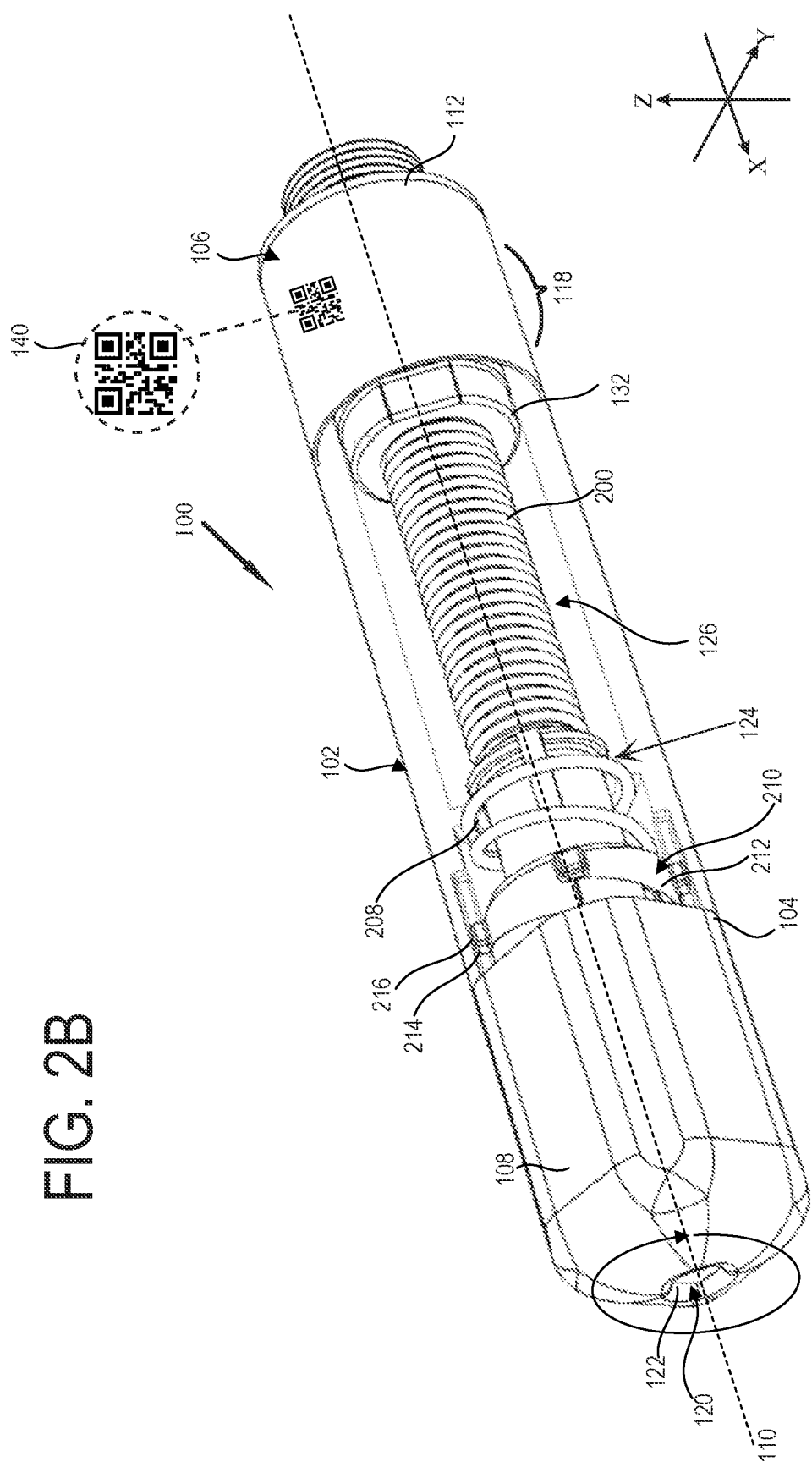

FIGS. 2A and 2B present perspective views of MDSV 100 in accordance with yet another embodiment. As with FIGS. 1A and 1B described above, FIG. 2A represents an initial state of MDSV 100 with the reservoir 114 essentially full of liquid concentrate 116. In FIG. 2B, the mouthpiece 108 has been rotated many times and the screw shaft 130 is now exposed to further illustrate that the screw plunger 126 has advanced down such that the threaded shaft of the screw plunger is now exposed to further illustrate that the rotation driven dispenser has advanced down and expelled substantially all of the liquid concentrate 116 from the reservoir 114—the MDSV 100 now being in a depleted state.

It will also be appreciated that in FIG. 2A the threads 200 of the screw shaft 130 are visible and pass through the reservoir 114. In contrast to the embodiment of MDSV 100 depicted in FIGS. 1A and 1B, the alternative embodiment of MSDV 100 depicted in FIGS. 2A and 2B does not have a spacer 144. FIG. 1A also illustrates a shutter 202 disposed at the distal end 204 of the screw shaft 130. As is described in greater detail below with respect to FIGS. 3, 4A-4C and 6, the shutter 202 has at least one shutter fin 206 and operates to expose and seal an aperture 128, presently shown in dotted relief as it is below a shutter fin.

As noted, it is again understood and appreciated, that the rotation of the mouthpiece 108 is limited to one direction: that is, for at least one embodiment the mouthpiece 108 can only be rotated clockwise, such that the metered rotation driven dispenser 124 cannot be backed up. Of course, for at least one alternative embodiment, the mouthpiece 108 can also be configured for counter-clockwise rotation to drive the metered rotation driven dispenser 124. Moreover, the rotation may be either clockwise or counter-clockwise, but not both.

Insurance of one-way rotation/anti-backturn advantageously further permits consistent and repeatable dispensation of the intended metered dose of liquid concentrate 116. Of course, alternative tactile or audible indicators and one-way rotation elements, such as but not limited to ratchets, may also be employed to inform the user of each proper rotation, or fraction thereof and/or assure one-way rotation.

As may also be appreciated in FIGS. 2A and 2B, for the embodiment of MDSV 100 as depicted, the engagement of the mouthpiece 108 to the screw shaft 130 further involves a spring 208 to provide an expansive force between the mouthpiece 108 and the general housing 102. For at least one embodiment, the dosing vaporizer system may also include an indicator structed and arranged to indicate to the user that he or she has rotated the mouthpiece a predetermined amount. Such an indicator may be a clicker—producing an audible click, and or vibration as a haptic indicator.

For at least one embodiment, a ratchet 210 may be employed to achieve one-direction rotation as well as to provide the tactile and/or audible indicator for proper rotation of the mouthpiece 108 relative to the housing 102. As is shown in FIGS. 2A and 2B, the rachet 210 has a plurality of spring elements 212 with blocking elements 214 at their distal ends. A corresponding set of blocking receivers 216 (such as but not limited to semi rectangular indents) are formed in the internal sidewall of the housing.

For the direction in which rotation is permitted, either or both the blocking elements 214 and blocking receivers 216 are structured and arranged to permit the blocking elements 214 to slide up and out of the blocking receivers 216 as the mouthpiece 108 is rotated. For the direction in which rotation is not permitted either or both the blocking elements 214 and blocking receivers 216 are structured and arranged to prevent the blocking elements 214 from sliding up and out. For example, to permit rotation to occur between the mouthpiece 108 and housing 102, the corresponding side of the blocking peg 214 and or blocking receivers 216 may be sloped to permit the blocking elements 214 to slide up and out.

In at least one embodiment the blocking elements 214 are the distal end of each spring element 212. For yet another embodiment, a peg, block or other element may be further formed at or otherwise connected to the distal end of each spring element.

For yet another embodiment, there may be one or more internal ridges or elevation points disposed adjacent to one end of the spring 208 such that the mouthpiece 108 and housing 102 are rotated relative to one another, the spring is compressed during part of the rotation as the coil slides over a ridge and then released as the end passes beyond the internal ridge, providing a click and/or tactile sensation that an interval of rotation has been achieved, corresponding to the delivery of a metered amount of oil/concentrate. For at least one embodiment, the rising and falling of the spring passing over one or more internal ridges may also ensure one-way rotation, for if rotation is attempted in reverse, the end of the spring abuts into an internal ridge and halts rotation.

Figure 7:
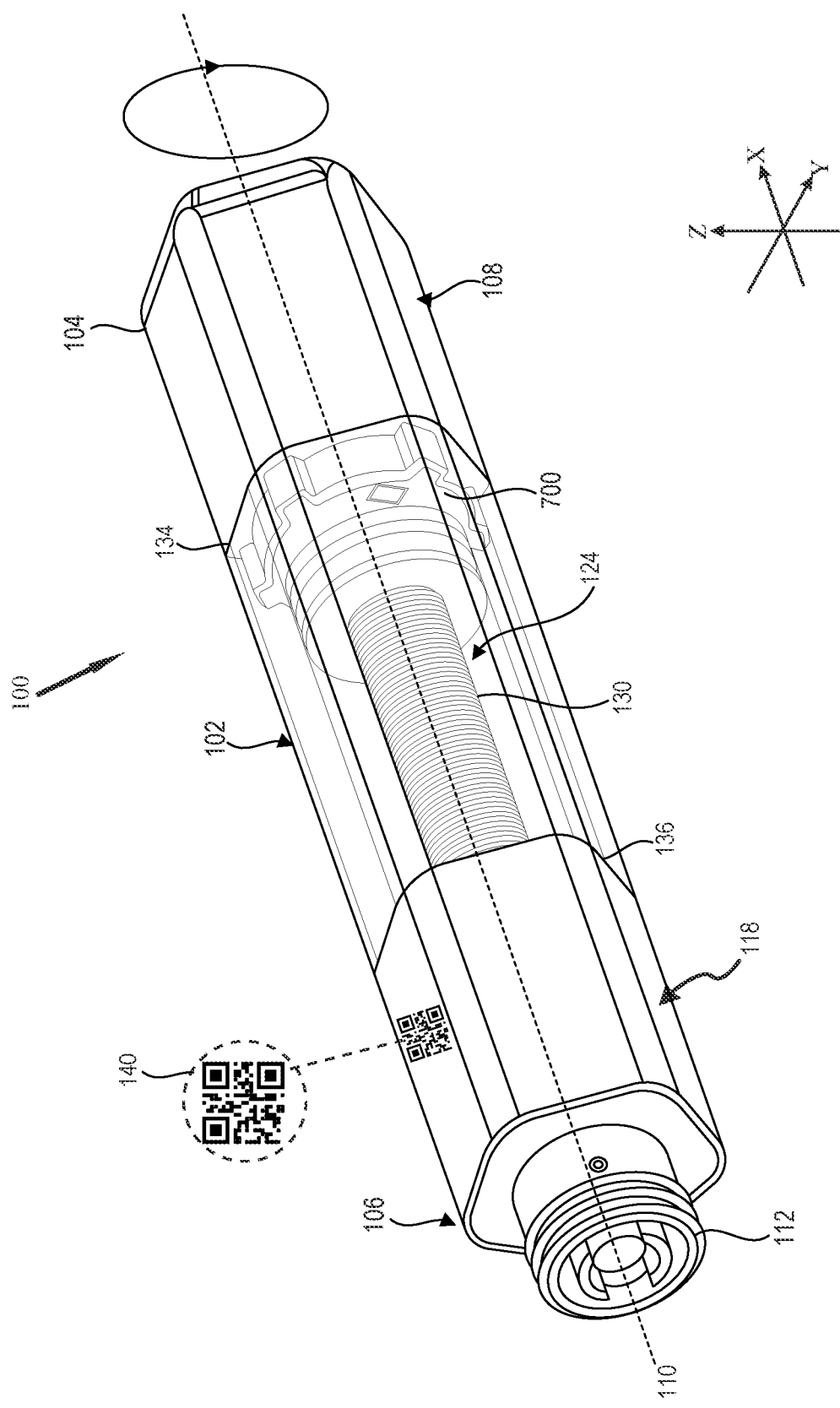
FIG. 7 presents yet another embodiment of Metered Dosing System Vaporizer having a non-circular cross section in accordance with at least one embodiment of the present invention.

For at least one alternative embodiment such a clicker may be provided by including a click plate between the mouthpiece 108 and the first end 104 of the housing 102, the rotation of the mouthpiece in relation to the click plate driving one or more spring loaded balls, or spring biased pins such that they click/hit/impact another surface as relative rotation places them up and over the tabs of a click plate. Such a click plate is shown in the alternative embodiment presented in FIG. 7 and the exploded view thereof of FIG. 8 corresponding to an alternative embodiment of a MDSV 100 as shown in FIG. 7.

Figure 2C:
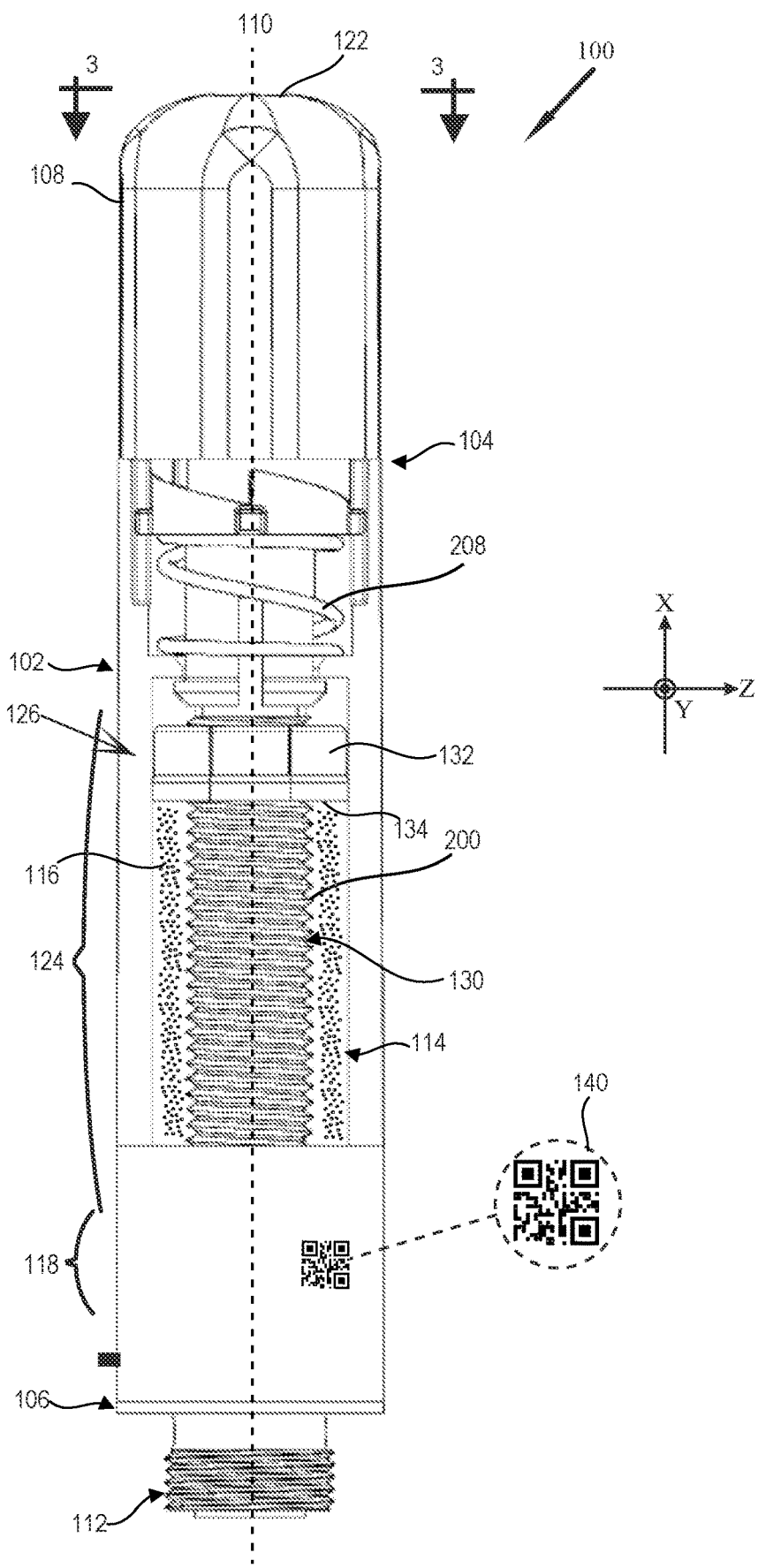
FIG. 2C illustrates a side view of the Metered Dosing System Vaporizer as shown in FIG. 2A in accordance with at least one embodiment of the present invention.
Figure 3:
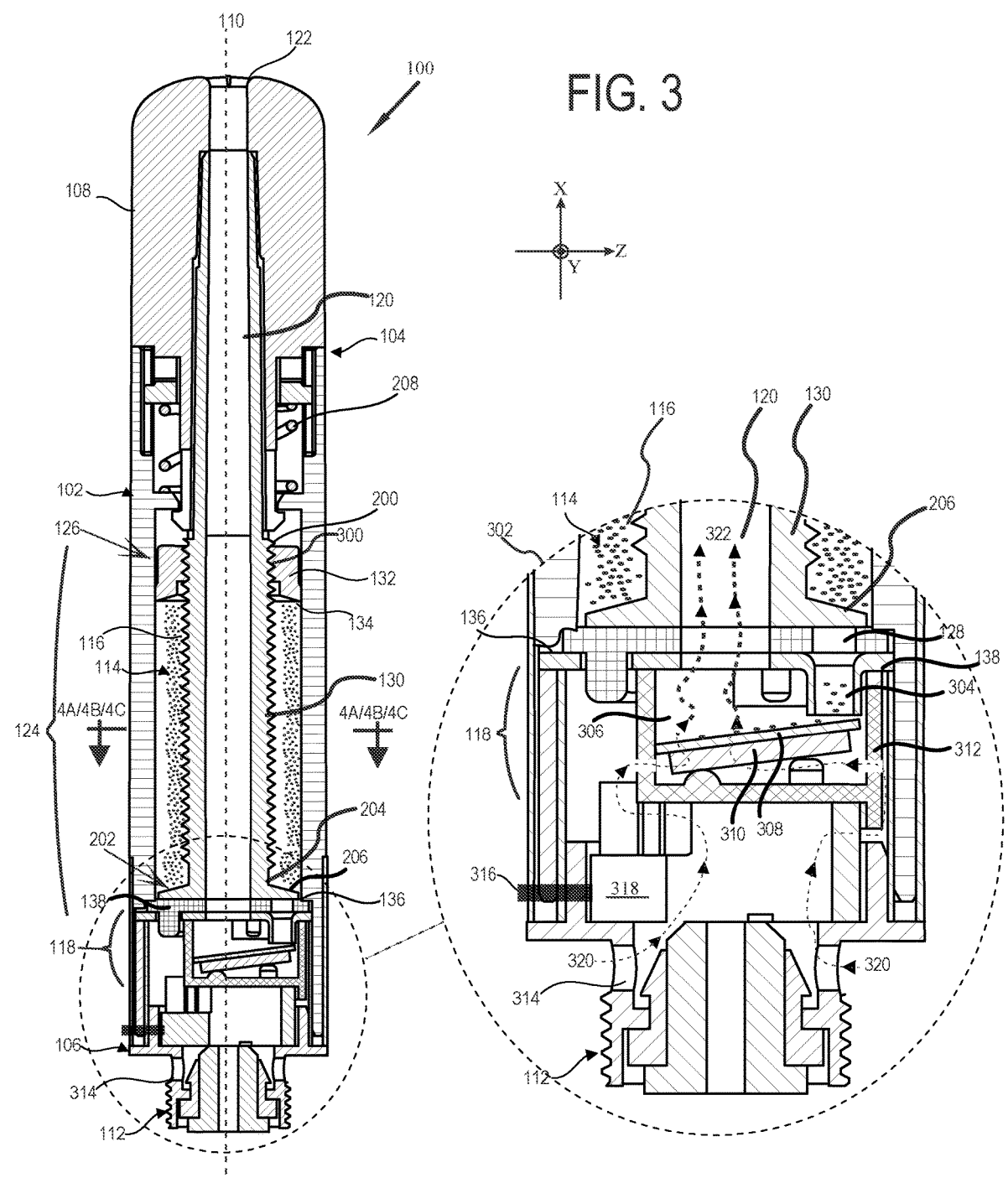
FIG. 3 presents a cut through illustration of a Metered Dosing System Vaporizer and more specifically the metered rotation driven dispenser and the thermally isolated vaporization chamber in accordance with at least one embodiment of the present invention.

FIG. 2C is a side view corresponding to the embodiment of MDSV 100 as shown in FIG. 2A. FIG. 3 is a cross section view of MDSV 100 as shown in FIG. 2C. As is further illustrated and described with respect to FIGS. 3-6, and especially FIG. 3 presenting a cross section view of at least one embodiment for a MDSV 100, the metered rotation driven dispenser 124 as shown in may be summarized as a screw plunger 126 structured and arranged to drive the liquid concentrate 116 from the reservoir 114 through at least one aperture 128 or valve and into the vaporizer 118. More specifically, the screw plunger 126 is provided by at least a screw shaft 130 and a plunger seal 132.

Moreover, it will be appreciated that the screw plunger 126 is operable to apply a predetermined force upon the reservoir 114 to dispense through the at least one aperture 128 or valve a predetermined amount of liquid concentrate into the vaporizer. More specifically, the rotation of the mouthpiece 108 induces a degree of rotation to the screw plunger 126, and more specifically the screw shaft 130. The degree of rotation is pre-determined to advance the plunger seal 132 against the liquid concentrate 116 of the reservoir 114 to dispense the predetermined amount of the liquid concentrate. For at least one alternative embodiment, the screw plunger 126 may provide external pressure against a reservoir 114 in the form of a bag or otherwise collapsible housing such that the moving end of the plunger does not directly encounter the liquid concentrate 116, but rather compresses the outside of the reservoir 114.

For at least one embodiment, the mouthpiece 108 is coupled directly to the metered rotation driven dispenser 124. More specifically, for at least one embodiment the degree of rotation imparted to the mouthpiece 108 is the same degree of rotation imparted to the screw shaft 130. For yet another embodiment, a coupling drive system may be employed such that there is a translation of the degree of rotation of the mouthpiece 108 and the resulting rotation of the screw shaft 130.

For at least one embodiment, the rotation driven dispenser 124 is a cycloidal gear assembly as is set forth and described in the '665 Patent and the '666 Patent each incorporated herein by reference. Moreover, for at least one embodiment, cycloidal gear assembly provides advantageously high gear ratio (e.g., revolutions between the rotating mouthpiece 108 and the rotation of the screw shaft 130 to impart lateral motion to the plunger seal 132, with low friction, high torque, compact size and excellent wear resistance—desirable characteristics facilitating consistent extrusion of liquid concentrate 116 for consistent metered dosing.

Those skilled in the art will appreciate that a cycloidal gear assembly is a form of toothed gear assembly based on epicycloid and hypocycloid curves generated by a circle rolling around the outside or inside of another circle. When two toothed gears engage, an imaginary circle—the pitch circle—can be drawn around the center of either gear through the point of contact between their respective teeth. The curves of the teeth outside the pitch circle are known as the addenda and the curves of the tooth spaces inside the pitch circle are known as the dedenda. Moreover, the addendum of one gear rests inside the dedendum of the other gear. The addenda of the wheel teeth are convex epi-cycloidal and the dedenda of the pinion are concave hypocycloidal curves generated by the same generating circle. This ensures that the motion of one gear is transferred to the other at a locally consistent angular velocity.

For at least one alternative embodiment, the rotation driven dispenser 124 is adapted from one or more embodiments of the screw plunger embodiment of the vaporizing cartridge with diffuser as is set forth and described in '062 App for System and Method For Vaporizing Cartridge System With Diffuser (incorporated by reference).

For at least one embodiment, the plunger seal 132 forms or at least partially defines the upper end, or first end 134, of the reservoir 114 opposite from the at least one aperture 128 or valve in the second end 136. In addition, for at least one embodiment, the plunger seal 132 has corresponding threads 300 (see FIG. 2, not shown in FIGS. 1A & 1B) to mate with the threads 202 the screw shaft 130.

It will be understood and appreciated that the pitch of the threads, or thread count per measured unit—Imperial (inches) or Metric (centimeters)—is preselected such that each quarter, half or full rotation of the mouthpiece 108 results in a known and intended linear advancement of the plunger seal 132.

For at least one embodiment, the plunger seal 132 has an alignment element structured and arranged to keep the plunger seal 132 from rotating within the housing as the screw shaft 130 is rotated. Moreover, the alignment element ensures that as the screw shaft 130 rotates through the plunger seal 132, the corresponding threads 300 and 202 ensure that the plunger seal 132 is driven towards the second end 136 of the reservoir 114. For at least one embodiment, the alignment element is the cross-section geometry of the plunger seal 132 and the housing 102 (e.g., non-circular). More specifically, the plunger seal 132 and the inside of the housing 102 may be formed with corresponding ovality, or ovalness, e.g., corresponding non-circular shapes that permits the plunger seal 132 to move longitudinally within the housing 102 without freely rotating. For yet another embodiment, the alignment element may be a rail and grove arrangement as between the plunger seal 132 and the housing 102.

Those skilled in the art will also realize and appreciate that changes to the thread pitch/thread count may be coordinated with the dimensions of the reservoir to advantageously provide precise metered dosing. More specifically, the same screw shaft 130 may be used with multiple MDSV 100 systems, however to accommodate proper product dosing between different MDSV 100 systems having different liquid concentrates, the dimensions of each respective reservoir 114 may be intentionally adjusted such that the same linear advancement of the plunger seal 132 results in an intentionally different, but predetermined quantity of different liquid concentrates being dispensed.

It is also to be appreciated that by physical space or a physical isolator component such as thermal isolator 138—such as insulation material—the vaporizer 118 is generally thermally isolated from the reservoir 114 of liquid concentrate 116. As such, the processes of vaporizing the dispensed quantity of liquid concentrate 116 does not adversely impact (e.g., heat) the liquid concentrate 116 within the reservoir 114, which may result in undesirable degradation or change to the liquid concentrate 116. In other words, it will be understood and appreciated that the liquid concentrate 116 is stored/located in the reservoir 114 that is physically removed and/or physically isolated from the vaporizer 118 such that heat as applied for the process of vaporization to dispensed liquid concentrate, the heat is not transmitted to the remaining liquid concentrate 116 contained in the reservoir 114.

Such isolation may be achieved by physical separation, thermal shielding, insulation or the transition of materials. It is of course understood and appreciated that as the dosing vaporizer system is a small and integrated device, some percentage of heat transfer may occur from the vaporizer 118 to the reservoir 114. However, for purposes of this disclosure and the embodiments contemplated hereunder, thermal isolation between the reservoir 114 and the vaporizer 118 is understood and appreciated to be those conditions where any heat transfer that does occur between reservoir 114 and the vaporizer 118 (and most specifically the vaporizing chamber shown and described in FIG. 2) has a substantially negligible effect upon the liquid concentrate 116 within the reservoir 114.

With respect to the above description, it will be understood and appreciated that a DVS 100 for at least one embodiment may be summarized as including: a housing 102 providing a first end 104 and opposite thereto a second end 106; a mouthpiece 108 disposed proximate to the first end 104, the mouthpiece 108 structured and arranged to rotate about the first end 104; an attacher 112 disposed proximate to the second end 106, the attacher 112 structured and arranged for removable attachment to a power source; a reservoir 114 of liquid concentrate 116 within the housing 102; a vaporizer 118 disposed proximate to the attacher 112 and thermally isolated from the reservoir 114; a vapor conduit 120 passing generally from the vaporizer, through the housing 102 to the mouthpiece 108; and a metered rotation driven dispenser structured and arranged to apply a predetermined force upon the reservoir 114 to dispense from the reservoir 114 into the vaporizer a predetermined amount of liquid concentrate 116, the metered rotation driven dispenser coupled to the mouthpiece 108.

Yet another embodiment of MDSV 100 may be summarized as including: a housing 102 providing a first end 104 and opposite thereto a second end 106; a mouthpiece 108 disposed proximate to the first end 104, the mouthpiece 108 structured and arranged to rotate about the first end 104; a 510 battery connector disposed proximate to the second end 106, the battery connector structured and arranged for removable attachment to a battery; a reservoir 114 of liquid concentrate 116 within the housing 102; a vaporizer 118 disposed proximate to the 510 battery connector and thermally isolated from the reservoir 114; a central vapor conduit 120 passing generally from the vaporizer, through the housing 102 to the mouthpiece 108; an aperture 128 disposed between the reservoir 114 and the vaporizer; and a screw plunger structured and arranged to apply a predetermined force upon the reservoir 114 to dispense from the aperture 128 a predetermined amount of liquid concentrate 116 into the vaporizer, the rotation of the mouthpiece 108 inducing a degree of rotation to the screw plunger, the degree of rotation pre-selected to advance the screw plunger 126 against the liquid concentrate 116 of the reservoir 114 to dispense the predetermined amount of the liquid concentrate 116.

As noted above, the aperture 128 may have a valve disposed therein, or a valve may be provided as a structure in place of the aperture 128. For at least one embodiment where a valve is provided within or in place of the aperture 128, the valve is at a first one-way valve. Varying embodiments may include a plurality of valves, and or one-way valves in parallel or series arrangement. Such configurations may be desired for ease of manufacturing, to better accommodate different liquid viscosities, to provide an airless pump chamber, or for other design parameters deemed beneficial for precise operation of the dosing vaporizer system.

For at least one embodiment, the aperture 128 is gated by a shutter 206—a mechanism or element structured and arranged to shut and open the aperture 128. Moreover, the shutter 206 allows liquid concentrate 116 to pass through the aperture 128 for a determined period of time before the aperture 128 is closed and the ability of the liquid concentrate 116 to pass, halted. In other words, the shutter 206 exposes the aperture 128 and then covers or otherwise seals the aperture 128. When exposed, the aperture 128 permits liquid concentrate 116 to be extruded therethrough so as to be deposited into the vaporizing chamber 306. When covered or closed, accidental or inadvertent leakage of the liquid concentrate 116 is essentially prevented such that liquid concentrate 116 does not inadvertently enter the vaporizing chamber 306 except in direct response to a dosing event.

For at least one embodiment the shutter 206 is provided by one or more shutter fins 208. For at least one embodiment, the distal end 204 of the screw shaft 130 may provide one or more shutter fins 208. More specifically, as the screw shaft 130 rotates, each shutter fin 208 rotates as well, and in so doing exposes and then seals each of the at least one aperture(s) 128 or valve(s), permitting the liquid concentrate 116 to be extruded from the reservoir.

The rotation of the screw shaft 130, and more specifically the movement of the shutter fins 208 is further shown in partial perspective views of MDSV 100 presented by FIGS. 3A, 3B and 3C. In FIG. 3A, shutter fin 208A is shown to be covering aperture 128 or valve. In FIG. 3B, the screw shaft 130 has been partially rotated such that shutter fin 208A is now removed from covering aperture 128 or valve, and shutter fin 208B has not yet rotated into place to cover aperture 128 or valve. In FIG. 3C, the screw shaft 130 has continued rotation and shutter fin 208B is now partially covering aperture 128 or valve. As the screw shaft 130 finishes the partial rotation, shutter fin 208B will assume the position of shutter fin 208A covering aperture 128 or valve as shown in FIG. 3A. Of course, other shutters 206 may be employed in varying embodiments that do not rely upon one or more shutter fins 208 extending from the screw shaft 130.

FIG. 3B also presents alternative embodiment options for a valve 400 disposed within aperture 128. In varying embodiments, valve 400 may be provided as a septum 402, or a more robust one-way valve 404 operating to allow the extrusion of liquid concentrate 116 from within the reservoir 114 when and as pressure is applied by the plunger seal 132 being advanced along the screw shaft 130 by rotation of the mouthpiece 108.

Moreover, as is shown in FIGS. 3A, 3B and 3C, an embodiment of MDSV 100 wherein the screw shaft 130 provides shutter fins 208, the liquid concentrate 116 may be simply extruded through aperture 128 when exposed. However, it will be understood and appreciated that valve 400 may be used in cooperation with a screw shaft 130 providing shutter fins 208, or in an alternative embodiment with a screw shaft 130 that does not provide shutter fins.

FIG. 4 presents an alternative embodiment for MDSV 100 wherein the screw shaft 130 does not provide shutter fins, and aperture 128 has been enhanced as a valve 400, and more specifically a septum 402.

As shown in FIG. 5, for at least one embodiment, the leading-edge 600 of each shutter fin 208 is angled up, such that as the rear portion is in flat contact with the bottom (second end 136) of the reservoir 114, such as the thermal isolator 138, the leading edge 600 is raised above the bottom (second end 136) of the reservoir 114 as indicated by dimension 602. Moreover, as the shutter fins(s) 208 rotates, the raised leading-edge scoops and directs liquid concentrate 116 into each of the at least one at least one aperture(s) 128 or valve(s), an action that may advantageously assist with the precise dispensation of the liquid concentrate 116.

With respect to FIG. 2 and especially the enlarged section 302 of MDSV 100, the location of thermal isolator 138 may also be appreciated for at least one embodiment. The thermal isolator 138 may also perform additional functions, such as also sealing the second end 136 of the reservoir 114 when each shutter fin 208 is disposed to cover each of the at least one at least one aperture(s) 128 or valve(s). For at least one embodiment the thermal isolator is a flexible material such as, but not limited to rubber or Teflon®. For at least one alternative embodiment the thermal isolator may be formed from but not limited to a glass, ceramic or composite material. In addition, the surface of the thermal isolator 138 exposed to the reservoir may be coated or treated with a smoothing/slickening agent.

It will also be appreciated that below the at least one aperture 128 or valve, is a port 304 structured and arranged to direct the extruded liquid concentrate 116 into the vaporizing chamber 306, and more specifically onto the diffuser element 308 which is disposed in thermal contact with a heater 310. For at least one embodiment, port 304 is provided by a metal element, such as stainless steel, which may be formed as an, or intended to further thermally isolate the reservoir 114 from the vaporizing chamber 306.

As is also shown in the enlarged section 302, the vaporizing chamber 306 is a substantially enclosed space defined by outer walls 312 that generally surround the vaporizing element such as the diffuser element 308 and thus substantially insulates the reservoir 114 and liquid concentrate 116 therein from detrimental heat exposure when the heater 310 is activated to achieve vaporization. More simply stated, the element(s) achieving vaporization within the vaporizing chamber 306 are configured achieve vaporization of the dispensed liquid concentrate 116 to properly and consistently, but these elements are also disposed in a specific location and isolated so as not to inadvertently degrade the un-dispensed liquid concentrate 116 remaining in the reservoir 114 thorough exposure to high temperatures. For at least one embodiment, the vaporizing chamber 306 may also have insulation between the heater 310 and the attacher 112 so as not to inadvertently heat the attached power support, such as a 510 battery.

For at least one embodiment the diffuser element 308 is structured and arranged to receive the liquid concentrate 116 and present it proximately to a heat source provided by the MDSV 100 such that the liquid concentrate 116 may be vaporized. Further still, for at least one embodiment the diffuser element 308 is a thermally conductive porous material. Surface tension of the liquid concentrate 116 and choice of materials, such as but not limited to metal, glass, ceramic or composite screens, perforated sheets, or woven constructs permit the diffuser element 308 to receive, and in at least one embodiment, wick the liquid concentrate across/throughout the diffuser element 308 to promote uniform and substantially consistent vaporization. It will be understood and appreciated that the use of capillary action within the vaporizing chamber to advantageously facilitate substantially complete vaporization is entirely different from, and unrelated to the active extrusion of the metered dose of a known quantity of liquid concentrate 116 as described above.

For at least one embodiment, the diffuser element 308 is metal, such as but not limited to gold, stainless steel, brass or tungsten steel. For another embodiment, the diffuser element 308 may be provided by metal plating/deposition upon a substrate. For yet another embodiment the diffuser element 308 is ceramic, glass or glass fiber. For still yet another embodiment, the diffuser element 308 is synthetic or organic fiber. It will also be understood and appreciated that as different embodiments of MDSV 100 may provide different liquid concentrates, different diffuser elements 308 may be specifically selected that are most suitable for the different liquid concentrates 116.

As such, MDSV 100 advantageously permits the most suitable diffuser element 308 to be paired with the liquid concentrate 116 of a given MDSV 100. In other words, for at least one embodiment the operation and efficiency of the MDSV 100 is improved as the need to provide a generic diffuser element suitable for many liquid concentrates, but not specifically optimized for one liquid concentrate is eliminated as each MDSV 100 provides its own optimized diffuser element 308.

It will also be noted that for at least one embodiment, the diffuser element 308 is angled relative to the longitudinal axis 110 of the MDSV 100 so as to further assist with the dispersal of the extruded liquid concentrate 116 for vaporization. In varying embodiments, the diffuser element 308 may also be disposed at least partially within a protective sleeve as a porous insert, the protective sleeve having a plurality of apertures, which in combination with pores within the porous insert permit air to flow through the diffuser element 308 thereby assisting in removing the resulting vapor and conducting it into the vapor conduit 120 for delivery from the opening in the mouthpiece 108 to the user.

It will be appreciated that, for at least one embedment, MDSV 100 provides one or more air intake ports 314 for the intake of air which is conducted into the vaporizing chamber 306. In varying embodiments, the air may be conducted through ports in the bottom of the vaporizing chamber 306, and/or the sidewalls of the vaporizing chamber 306. It will also be appreciated that in varying embodiments the air intake ports 314 may be protected with mesh or filter material so as to reduce the possible contamination of the vaporizing chamber and diffuser element 308 with foreign airborne particulates.

With respect to FIG. 2. it may also be appreciated that the vapor conduit 120 fluidly interconnecting the vaporizing chamber to the opening 122 in the mouthpiece 108 is substantially straight, providing no turns, bends or elements of redirection. As such it is appreciated that the vapor traveling through the vapor conduit 120 has minimal interaction with the sidewalls of the vapor conduit 120. As such, although for at least one embodiment the vapor conduit 120 passes centrally through the reservoir 114, there is a negligible transfer of heat from the passing vapor to the remaining liquid concentrate 116 within the reservoir 114. For at least one embodiment, the vapor conduit 120 may be structured and arranged to provide some measure of heat insulation between the vapor conduit and the reservoir through the choice of materials, dual wall construction, or combinations thereof. The vapor conduit 120 may also be coated internally or externally with an insulating material.

As is shown in the enlarged section of 302 of FIG. 2, air (represented as light dotted lines 320) has been illustrated entering through air intake ports 314. This air passes through internal passageways so as to be delivered proximate to the diffuser element 308. In varying embodiments these passages may be through the outer walls 312 or bottom of the vaporizing chamber 306. For at least one embodiment, the air 320 passes through the diffuser element 308 upon which has been dispensed a metered dose of liquid concentrate 116 (again represented as dots). As this liquid concentrate is vaporized, the air 320 becomes enriched (represented as heavy dotted lines 332), and continues through the vapor conduit 120 to the mouthpiece 108 where it is provided to the user.

With respect to FIG. 2 the nature of the attacher 112 for connecting the MDSV 100 to a power source, such as a 510 battery may also be further appreciated. Use of an external power supply may advantageously reduce the costs and complexity of manufacturing each MDSV 100, as well as ensure that external power sources are not wasted simply because the reservoir has been depleted, or that remaining concentrate is wasted upon the depletion of an internal power supply.

For at least one embodiment, the MDSV 100 may be dependent upon an external trigger, such as a button, that is provided as a component of the remote power supply for activation of the MDSV 100 to vaporize the metered dose of liquid concentrate disposed into the vaporizing chamber. For at least one embodiment, the MDSV 100 may further include an engager, such as a trigger switch that is reset with the rotation of the mouthpiece 108 and activation of the metered rotation driven dispenser 124, such a trigger preventing re-activation of the heating element when liquid concentrate has not been disposed into the vaporizing chamber.

For all embodiments described herein of MDSV 100, there is intended to be an activator, structured and arranged to activate the MDSV 100 by permitting an electrical connection between the MDSV 100, and more specifically heater 310 or other electrical device that is primarily responsible for transforming the predetermined amount of extruded liquid concentrate 116, and the and the power source (such as the 510 battery) for a first period of time, the power permitting the MDSV 100 to generate heat and vaporize the predetermined amount of extruded liquid concentrate 116.

In varying embodiments, the activator may be a component of the power source (such as the 510 battery) or the activator may be a component of the MDSV 100 itself, such as a push button 316.

Although the dosing vaporizer system as shown and described herein is generally intended for embodiments of stand-alone operation (when coupled to a power source), for at least one alternative embodiment, the MDSV 100 system may be further enhanced with a controller, e.g. control unit 318 having electrical circuitry with a processor configured and/or adapted to control the heat energy generated by the heater 310 to achieve vaporization of the metered dose of liquid concentrate 116 disposed into the vaporizing chamber 306.

For at least one embodiment, the control unit 318 may further include memory and/or wireless communication circuitry, e.g., a transceiver, that may interface with one or more external computing devices to receive instructions and/or parameters for operation. Moreover, for at least one embodiment, the processor of the control unit 318 is operable to interface with the vaporizing element, such as heater 310 or nebulizer, as well as the transceiver to provide operation characteristics such as but not limited to use cycle, duty cycle, remaining dosages, frequency of use, etc. The processor may be further operable to interface with the transceiver to receive parameters for use, such as heating duration and heating temperature or other operational characteristics that may be affected by the user's location, i.e., a dry climate vs. a humid climate.

The processor may also be operable to receive and/or confirm that the user is authorized to use the vaporizing device. For example, does the user have an account, are they of the proper age, do they have a prescription, has a sufficient time passed since the last activation, etc.

Indeed, for at least one embodiment, such further operational advantages may be facilitated by a remote application operating on a user's mobile device such as a smart phone (i.e., an iPhone®, Android® or another portable device). Such devices may further scan, read or otherwise obtain a unique marking or characteristic (e.g., QR code, RFID chip, barcode, serial number, etc.) that is provided by or upon the MDSV 100 as a unique identifier 140 (see FIGS. 1A & 1B) to provide unique identification of the vaporizing device and/or the liquid concentrate therein. For at least one embodiment, the unique identifier 140 may be encoded in the memory of the control unit as well as externally provided. The unique identifier 140 may also be associated with a user and/or the provider of the liquid concentrate for life cycle tracking, usage tracking, and or other data collecting and utilization efforts as may be desired to improve performance of MDSV 100, and/or the user's interactions therewith.

With such unique identification, the application can determine and/or specify various operational parameters for the vaporizing device, and/or further communicate with one or more remote systems (such as databases) to further confirm user identity through verification of the user account and/or local biometric data (picture, finger print, etc.), Global Positioning System "GPS" location and comparison for verification that use of the dosing vaporizer system is permitted (or not prohibited), and other such activities and features to improve and enhance the users experience and utility with the vaporizing system.

The remote computing device such as a smart phone (i.e., an iPhone®, Android® or other portable device), a remote application suitable and adaptable for controlling an embodiment of MDSV 100 with a control unit 318, and a remote database providing information relating to the unique identifier as may be determined by a user's computing device such as a smart phone, are detailed in the '967 Patent, the '674 Application, the '665 Patent, and '666 Patent, each incorporated herein by reference.

FIG. 7 presents an alternative embodiment of a MDSV 100, with clicker 700 disposed between the mouthpiece 108 and the housing 102. In contrast to the embodiment shown in FIGS. 1A and 1B, the housing 102 and mouthpiece 108 as shown in FIG. 4 have a different cross section geometry. Moreover, the cross section of the mouthpiece and housing may vary in different embodiments without departing from the scope of the present invention. Indeed, for at least one embodiment, it may be desirable for the housing 102 and the mouthpiece 108 to have non-circular cross sections, such that they may be more easily grasped by a user to facilitate the user's rotation of the mouthpiece 108 relative to the housing 102 to drive the metered rotation driven dispenser 124.

In addition, the orientation of MDSV 100 in FIG. 6 is reversed from that shown in FIGS. 1A and 1B. In this reversed orientation, the nature of the attacher 112 as a screw fitting for a 510 battery may be more fully appreciated.

Figure 8:
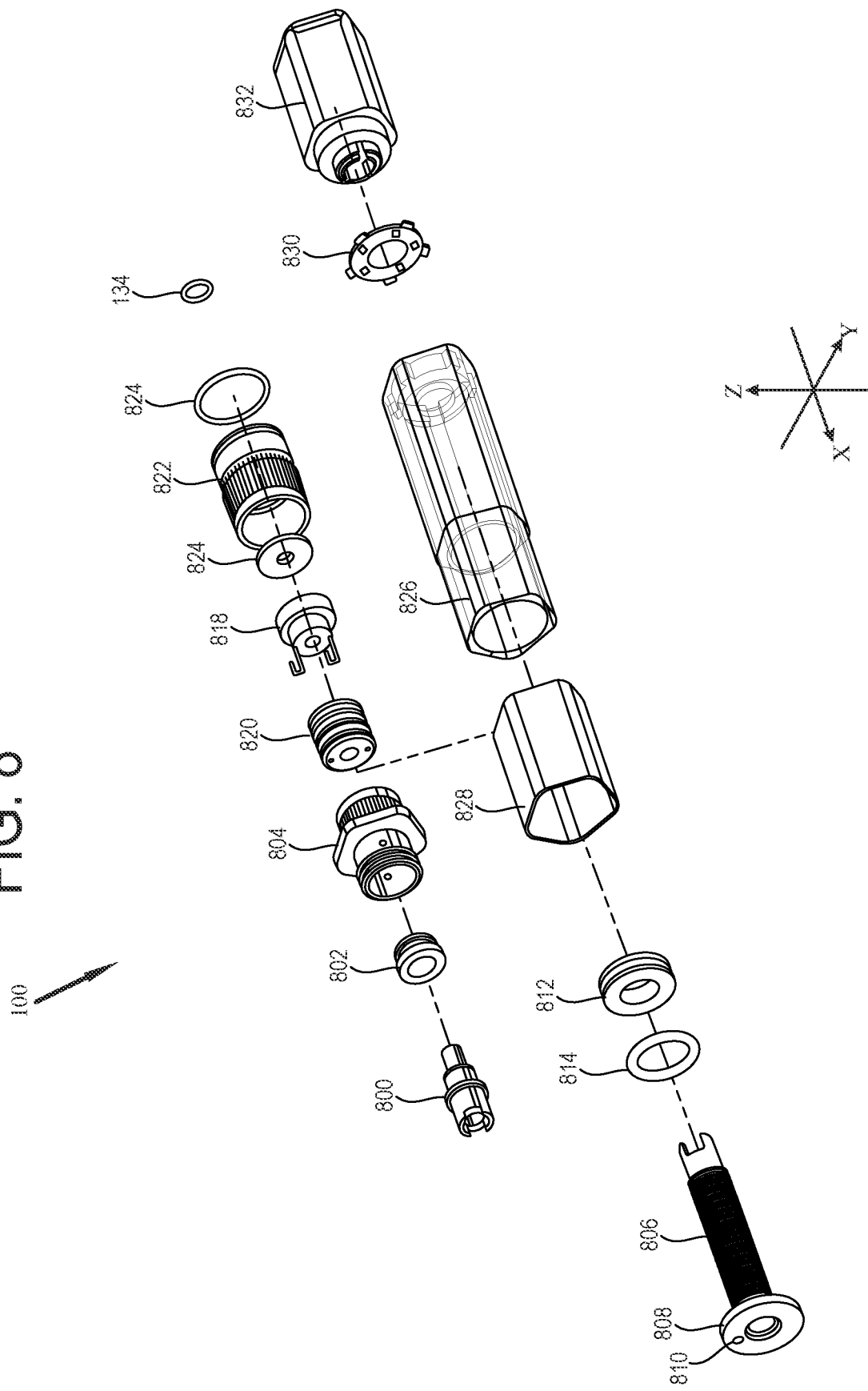
FIG. 8 presents an exploded view of the Metered Dosing System Vaporizer as shown in FIG. 6 in accordance with at least one embodiment of the present invention.

FIG. 8 presents a partially exploded view of the embodiment of the MDSV 100 as shown in FIG. 4. FIG. 8 should be understood and appreciated not to be a definitive presentation of the elements and components providing a MDSV 100, but rather as an overview of the general elements and components as may be utilized in providing at least one embodiment of a MDSV 100. Moreover, in FIG. 8, the base post 800, insulating gromet 802 and metallic screw base 804 of the 510 battery attacher base are shown, as is a screw shaft 130/806 disposed upon thermal isolator 138/808 having an aperture 128/810. A plunger seal 132/812 with outer 0-Ring seal 814 are engaged about the screw shaft 130/806.

An insulated vaporizing chamber assembly 816 providing appropriate electrical connections to the screw base 804, and incorporating a control unit (not shown) receives a ceramic heater 310/818 disposed within an insulating sleeve 820, and collective disposed in an outer metal and insulating housing 822 with one or more O-rings 824 to seal, support and isolate the vaporizing chamber assembly within the housing 102/826 of the MDSV 100. For the embodiment shown, an optional exterior metal collar 828 is also provided to be disposed about the housing 102/626 proximate to the vaporizer chamber assembly 816.

A click plate 830 is disposed between the housing 102/826 and the mouthpiece 108/832. The click plate may be further structured and arranged so as to permit only one-way rotation of the mouthpiece 108/832 relative to the housing 102/826. Such one-way rotation may be facilitated by the use of springs, spring teeth or arms, a ratchet element, or such other element as may be deemed appropriate in one or more embodiments. For at least one embodiment, the housing 102/826 is translucent, if not transparent, such that a user may visually observe the amount of liquid concentrate within the reservoir of the assembled MDSV 100.

Having disclosed various embodiments for MDSV 100 as described above with respect to FIGS. 1-8, it will be understood and appreciated that a method for vaporizing a product, such as liquid concentrate 116 may be performed with any of the above noted embodiments.

More specifically, according to at least one embodiment a method for vaporizing a product, is provided by: providing a housing 102 providing; a first end 104 and opposite thereto a second end 106; a mouthpiece 108 disposed proximate to the first end 104, the mouthpiece 108 structured and arranged to rotate about the first end 104; an attacher 112 disposed proximate to the second end 106, the attacher 112 structured and arranged for removable attachment to a power source; a reservoir 114 of liquid concentrate 116 within the housing 102; a vaporizer 118 disposed proximate to the attacher 112 and thermally isolated from the reservoir 114; an vapor conduit 120 passing generally from the vaporizer, through the housing 102 to the mouthpiece 108; a metered rotation driven dispenser structured and arranged to apply a predetermined force upon the reservoir 114 to dispense from the reservoir 114 into the vaporizer a predetermined amount of liquid concentrate 116, the metered rotation driven dispenser coupled to the mouthpiece 108; rotating the mouthpiece 108 to activate the metered rotation driven dispenser to dispense a predetermined amount of liquid concentrate 116 into the vaporizer; and activating the vaporizer to vaporize the dispensed liquid concentrate 116 into a vapor that is provided to a user through the mouthpiece 108.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A method for vaporizing a metered dosing of a product, comprising:

providing a metered dosing vaporizer system comprising
  a housing providing;
  a first end and opposite thereto a second end;
  a mouthpiece disposed proximate to the first end, the mouthpiece structured and arranged to rotate about the first end;
  an attacher disposed proximate to the second end, the attacher structured and arranged for removable attachment to a power source;
  a reservoir of liquid concentrate within the housing;
  a vaporizer disposed proximate to the attacher and thermally isolated from the reservoir;
  a vapor conduit passing generally from the vaporizer, through the housing to the mouthpiece;
  a metered rotation driven dispenser structured and arranged to apply a predetermined force upon the reservoir to dispense from the reservoir into the vaporizer a predetermined amount of liquid concentrate, the metered rotation driven dispenser coupled to the mouthpiece;
  rotating the mouthpiece to activate the metered rotation driven dispenser to dispense a predetermined amount of liquid concentrate into the vaporizer; and
  activating the vaporizer to vaporize the dispensed liquid concentrate into a vapor that is provided to a user through the mouthpiece.

2. The method of claim 1, wherein the metered rotation driven dispenser comprises:
  an aperture disposed between the reservoir and the vaporizer; and
  a screw plunger structured and arranged to apply a predetermined force upon the reservoir to dispense from the aperture a predetermined amount of liquid concentrate into the vaporizer, the rotation of the mouthpiece inducing a degree of rotation to the screw plunger, the degree of rotation pre-selected to advance the screw plunger against the liquid concentrate of the reservoir to dispense the predetermined amount of the liquid concentrate.

3. The method of claim 2, wherein the metered rotation driven dispenser further includes a cycloidal gear assembly to actuate the screw plunger against the reservoir of liquid concentrate to extrude the predetermined amount of the liquid concentrate.

4. The method of claim 2, wherein the aperture is gated by a shutter.

5. The method of claim 4, wherein the screw plunger further provides at least one shutter fin structured and arranged to alternatively cover and expose the aperture as the screw plunger is rotated.

6. The method of claim 5, wherein the at least one shutter fin as a raised leading edge providing an angled surface to direct liquid concentrate into the aperture as the screw plunger is rotated.

7. The method of claim 2, wherein the aperture is a one way valve.

8. The method of claim 2, wherein the attacher is a 510 battery connector.

9. The method of claim 2, wherein the vaporizer comprises a thermally conductive porous material for receiving the dispensed predetermined amount of liquid concentrate, and an electric heater proximate to the thermally conductive porous material, the electric heater operable to vaporize the predetermined amount of liquid concentrate.

10. The method of claim 2, wherein the metered dosing vaporizer system further includes an audible indicator structured and arranged to produce an audible indication that a predetermined dosage of liquid concentrate has been extruded from the reservoir, by activation of the metered rotation driven dispenser.

11. The method of claim 2, wherein the metered dosing vaporizer system further includes a unique identifier permitting unique identification of the dosing vaporizer system and determination of the liquid concentrate.

12. The method of claim 11, wherein the metered dosing vaporizer system further includes a control unit, the control unit operable to confirm a user as authorized to use the vaporizing device based at least in part on the unique identifier.

13. A metered dosing vaporizer system comprising:
  a housing providing a first end and opposite thereto a second end;
  a mouthpiece disposed proximate to the first end, the mouthpiece structured and arranged to rotate about the first end;
  an attacher disposed proximate to the second end, the attacher structured and arranged for removable attachment to a power source;
  the housing at least partially enclosing:
    a reservoir of liquid concentrate;
    a vaporizer disposed proximate to the attacher and thermally isolated from the reservoir;
    a vapor conduit coupling the vaporizer to the mouthpiece; and
    a metered dispenser structured and arranged to dispense from the reservoir into the vaporizer a predetermined amount of liquid concentrate upon a pre-selected degree of rotation of the mouthpiece.

14. The metered dosing vaporizer system of claim 13, further including an activator, structured and arranged to activate the vaporizer by permitting a connection between the vaporizer and the power source for a first period of time, the power permitting the vaporizer to generate heat and vaporize the predetermined amount of liquid concentrate dispensed.

15. The metered dosing vaporizer system of claim 13, wherein the metered dispenser comprises:
  a screw plunger provided at least in part by a rotatable shaft disposed generally about the longitudinal axis, the rotatable shaft having a first end in mechanical connection with the mouthpiece, and a second portion in mechanical connection with a plunger seal disposed at a first end of the reservoir of liquid concentrate opposite from the vaporizer;
  an aperture opposite from the plunger seal and disposed between the reservoir and the vaporizer; and
  wherein the rotatable shaft is structured and arranged to move the plunger seal towards the vaporizer, applying a predetermined force upon the reservoir to dispense the predetermined amount of liquid from the one-way valve into the vaporizer.

16. The metered dosing vaporizer system of claim 15, wherein the aperture is gated by a shutter.

17. The metered dosing vaporizer system of claim 16, wherein the screw plunger further provides at least one shutter fin structured and arranged to alternatively cover and expose the aperture as the screw plunger is rotated.

18. The metered dosing vaporizer system of claim 17, wherein the at least one shutter fin as a raised leading edge providing an angled surface to direct liquid concentrate into the aperture as the screw plunger is rotated.

19. The metered dosing vaporizer system of claim 13, wherein the metered dosing vaporizer system further includes an audible indicator structured and arranged to produce an audible indication that a predetermined dosage of liquid concentrate has been extruded from the reservoir, by activation of the metered dispenser.

20. The metered dosing vaporizer system of claim 13, further including a unique identifier permitting unique identification of the dosing vaporizer system and determination of the liquid concentrate.

21. The metered dosing vaporizer system of claim 20, further including a control unit disposed within the housing and configured to read the unique identifier, the control unit further configured to control the heating element to generate heat based on the determination of the liquid concentrate.

22. The metered dosing vaporizer system of claim 20, further including a control unit disposed within the housing and configured to read the unique identifier, the control unit in operable control of a communication unit configured to transmit the unique identifier to a remote computing device, the remote computing device providing the unique identifier to a central server having a database; wherein the central server is structured and arranged to:
 receive the unique identifier from the remote computing device;
 match the unique identifier to the same unique identifier in the database;
 retrieve concentrate information corresponding to the matched unique identifier from the database; and
 transmit the concentrate information to the remote computing device.

23. The metered dosing vaporizer system of claim 22, wherein an absence of a match to the same unique identifier in the database prevents activation of the metered dosing vaporizer system.

24. A metered dosing vaporizer system comprising:
 a housing providing a first end and opposite thereto a second end;
 a mouthpiece disposed proximate to the first end, the mouthpiece structured and arranged to rotate about the first end;
 an attacher disposed proximate to the second end, the attacher structured and arranged for removable attachment to a power source;
 a reservoir of liquid concentrate within the housing;
 a vaporizer disposed proximate to the attacher and thermally isolated from the reservoir;
 a vapor conduit passing generally from the vaporizer, through the housing to the mouthpiece;
 a metered rotation driven dispenser structured and arranged to apply a predetermined force upon the reservoir to dispense from the reservoir into the vaporizer a predetermined amount of liquid concentrate, wherein the metered rotation driven dispenser is coupled to the mouthpiece;
 a wireless transceiver structured and arranged for wireless communication with at least one remote computing device; and
 a control unit having a processor configured to control the vaporizer for the vaporization of the dispensed liquid concentrate and to control a wireless transceiver structured and arranged for wireless communication with at least one remote computing device, the control unit receiving by the wireless transceiver at least parameters for operation from the at least one remote computing device.

25. The metered dosing vaporizer system of claim 24, further comprising:
 a remote server system having a processor and a database;
 at least one remote application for installation upon a remote computing device having a processor and a second wireless transceiver controlled by the processor, the second wireless transceiver structured and arranged for wireless communication with the metered dosing vaporizer system and the remote server system;
 wherein in response to a user indicating a desire for a vaporization event to the remote application, the remote computing device communicating with the database of the remote server to confirm the user as authorized for the vaporization event, and in response to authorization, communicating with the dosing vaporizer system to permit the control unit to control vaporization of the dispensed liquid concentrate.

26. The metered dosing vaporizer system of claim 24, further including a unique identifier permitting unique identification of the dosing vaporizer system and determination of the liquid concentrate.

27. The metered dosing vaporizer system of claim 24, wherein the control unit is further configured to communicate the unique identifier by the wireless transceiver to a remote computing device, the remote computing device providing the unique identifier to a central server having a database; wherein the central server is structured and arranged to:
 receive the unique identifier from the remote computing device;
 match the unique identifier to the same unique identifier in the database;
 retrieve liquid concentrate information corresponding to the matched unique identifier from the database; and
 transmit the liquid concentrate information to the remote computing device.

28. The metered dosing vaporizer system of claim 27, wherein an absence of a match to the same unique identifier in the database prevents activation of the metered dosing vaporizer system.

29. The metered dosing vaporizer system of claim 24, wherein the metered rotation driven dispenser comprises:
 an aperture disposed between the reservoir and the vaporizer; and
 a screw plunger structured and arranged to apply a predetermined force upon the reservoir to dispense from the aperture a predetermined amount of liquid concentrate into the vaporizer, the rotation of the mouthpiece inducing a degree of rotation to the screw plunger, the degree of rotation pre-selected to advance the screw plunger against the liquid concentrate of the reservoir to dispense the predetermined amount of the liquid concentrate.

30. The metered dosing vaporizer system of claim 29, wherein the aperture is gated by a shutter.

31. The metered dosing vaporizer system of claim 30, wherein the screw plunger further provides at least one shutter fin structured and arranged to alternatively cover and expose the aperture as the screw plunger is rotated.

32. The metered dosing vaporizer system of claim 31, wherein the at least one shutter fin has a raised leading edge providing an angled surface to direct liquid concentrate into the aperture as the screw plunger is rotated.

33. The metered dosing vaporizer system of claim 24, wherein the mouthpiece is structured and arranged for one way rotation.

34. The metered dosing vaporizer system of claim 24, further including an audible indicator structured and arranged to produce an audible indication that a predetermined dosage of liquid concentrate has been extruded from the reservoir, by activation of the metered rotation driven dispenser.

* * * * *